US010773194B2

(12) United States Patent
Trampler et al.

(10) Patent No.: US 10,773,194 B2
(45) Date of Patent: Sep. 15, 2020

(54) METHODS, SYSTEMS, AND APPARATUSES FOR ACOUSTICALLY SEPARATING AND WASHING PARTICLES

(71) Applicant: SONOSEP TECHNOLOGIES INC., Vancouver (CA)

(72) Inventors: Felix Trampler, Hinterbruehl (AT); James Piret, Vancouver (CA)

(73) Assignee: SONOSEP TECHNOLOGIES INC., Vancouver (CA)

( * ) Notice: Subject to any disclaimer, the term of this patent is extended or adjusted under 35 U.S.C. 154(b) by 191 days.

(21) Appl. No.: 15/767,680

(22) PCT Filed: Oct. 12, 2016

(86) PCT No.: PCT/CA2016/051188
§ 371 (c)(1),
(2) Date: Apr. 12, 2018

(87) PCT Pub. No.: WO2017/063080
PCT Pub. Date: Apr. 20, 2017

(65) Prior Publication Data
US 2018/0296954 A1 Oct. 18, 2018

Related U.S. Application Data

(60) Provisional application No. 62/241,341, filed on Oct. 14, 2015.

(51) Int. Cl.
*B01D 43/00* (2006.01)
*B08B 3/12* (2006.01)
(Continued)

(52) U.S. Cl.
CPC ........... *B01D 43/00* (2013.01); *B01D 21/283* (2013.01); *B08B 3/12* (2013.01); *C12M 47/02* (2013.01); *C12M 47/12* (2013.01); *G10K 11/04* (2013.01)

(58) Field of Classification Search
CPC ........ B01D 21/283; B01D 43/00; B08B 3/12; B01J 8/005; B01J 8/007; B01J 19/10; C12M 47/02; C12M 47/12
See application file for complete search history.

(56) References Cited

U.S. PATENT DOCUMENTS

| 4,743,361 A | 5/1988 | Schram |
| 5,527,460 A | 6/1996 | Trampler et al. |

(Continued)

FOREIGN PATENT DOCUMENTS

| CA | 2679042 A1 | 9/2008 |
| EP | 1365849 A1 | 12/2003 |

(Continued)

OTHER PUBLICATIONS

Extended European Search Report in European Patent Application No. 16854678.6, dated Sep. 5, 2019.

(Continued)

*Primary Examiner* — Lessanework Seifu
(74) *Attorney, Agent, or Firm* — Adrienne Bieber McNeil; ABM Intellectual Property Inc.

(57) ABSTRACT

A method of washing particles in an acoustic chamber includes (a) flowing a suspension of particles in a suspension medium through a standing wave generated in a standing wave volume of the acoustic chamber to accumulate within the acoustic chamber at least some of the particles as raw particle concentrate; and (b) flowing a wash medium through the acoustic chamber to wash within the acoustic chamber at least some of the particles of the raw particle concentrate, and retaining within the acoustic chamber at least some washed particles.

18 Claims, 10 Drawing Sheets

(51) Int. Cl.
     *C12M 1/00*        (2006.01)
     *B01D 21/28*      (2006.01)
     *G10K 11/04*      (2006.01)

(56) References Cited

U.S. PATENT DOCUMENTS

| | | |
|---|---|---|
| 5,626,767 A | 5/1997 | Trampler et al. |
| 2004/0142463 A1 | 7/2004 | Walker et al. |
| 2014/0377834 A1* | 12/2014 | Presz, Jr. ............... C12M 47/02 435/173.9 |
| 2015/0111277 A1 | 4/2015 | Hamman et al. |
| 2015/0209696 A1 | 7/2015 | Kambayashi et al. |

FOREIGN PATENT DOCUMENTS

| | | |
|---|---|---|
| WO | 02072236 A1 | 9/2002 |
| WO | 9832516 A1 | 9/2019 |

OTHER PUBLICATIONS

International Search Report and Written Opinion from PCT/CA2016/051188.

Technical Data Sheet STS90. Biosep: the advanced acoustic cell retention device. Oct. 2002.

* cited by examiner

METHODS, SYSTEMS, AND APPARATUSES FOR ACOUSTICALLY SEPARATING AND WASHING PARTICLES

CROSS-REFERENCE TO RELATED APPLICATION

This application is a national stage entry of International Application No. PCT/CA2016/051188, filed on Oct. 12, 2016, which claims priority from U.S. Provisional Patent Application 62/241,341, filed on Oct. 14, 2015, both of which are incorporated herein by reference in their entirety.

FIELD

The disclosure relates to methods of washing particles in an acoustic chamber, and acoustic chamber systems and apparatuses for washing particles.

BACKGROUND

U.S. Pat. Nos. 5,527,460 and 5,626,767 (Trampler et al.) purport to disclose separating and recycling particulate material suspended in a fluid by means of an ultrasonic resonance wave. In a preferred embodiment, the ultrasonic resonance field is generated within a multilayered composite resonator system including a transducer, the suspension and a mirror parallel to each other. Dimensions and frequencies resonant to the whole system but not exciting Eigen-frequencies of transducer and mirror itself are chosen so that thermal dissipation is minimized. Generally, the process is purported to be suitable for all kinds of particles (solid, liquid or gaseous disperse phases) especially for hydrosols (particles in water) and for separation of biological particles such as mammalian, bacterial and plant cells or aggregates. Specialized applications in biotechnology are described including an acoustic filter for mammalian cell bioreactors or the selective retention of viable cells relative to non-viable cells.

SUMMARY

The following summary is intended to introduce the reader to various aspects of the specification, but not to define any invention.

According to some aspects, a method of washing particles in an acoustic chamber includes: (a) flowing a suspension of particles in a suspension medium through a standing wave generated in a standing wave volume of the acoustic chamber to accumulate within the acoustic chamber at least some of the particles as raw particle concentrate; and (b) flowing a wash medium through the acoustic chamber to wash within the acoustic chamber at least some of the particles of the raw particle concentrate, and retaining within the acoustic chamber at least some washed particles.

In some examples, some particles of the raw particle concentrate settle within a settling volume of the acoustic chamber. The settling volume is located below the standing wave volume.

In some examples, some of the washed particles settle within the settling volume.

In some examples, during step (b) at least some of the washed particles are resuspended in the wash medium as resuspended particles, and step (b) further includes flowing the wash medium and the resuspended particles through the standing wave to retain the resuspended particles within the acoustic chamber.

In some examples, the acoustic chamber includes a first bottom port below the settling volume and a top port above the standing wave volume, and during step (b), the wash medium flows through the acoustic chamber from the first bottom port to the top port through the raw particle concentrate.

In some examples, the acoustic chamber includes at least one second bottom port spaced apart from the first bottom port, and during step (b), the wash medium flows through the acoustic chamber from the second bottom port to the top port through the raw particle concentrate.

In some examples, during step (b), the wash medium flows into the raw particle concentrate through the first bottom port in a first direction and through the second bottom port in a second direction different from the first direction.

In some examples, the second bottom port is above the first bottom port.

In some examples, during step (a), the suspension medium flows through the acoustic chamber from the first bottom port to the top port through the standing wave.

In some examples, step (a) occurs prior to step (b). In some examples, step (a) and step (b) occur simultaneously.

In some examples, the acoustic chamber includes a side port above the settling volume, and during step (a), the suspension medium flows through the acoustic chamber from the side port to the top port through the standing wave.

In some examples, the method further includes, after step (a) and prior to step (b), evacuating at least some supernatant suspension medium from the acoustic chamber, and replacing the evacuated supernatant suspension medium with the wash medium.

In some examples, the suspension medium is evacuated from the acoustic chamber through a side port above the settling volume.

In some examples, the wash medium flows into the acoustic chamber through the side port to replace the evacuated suspension medium.

In some examples, the method further includes, after step (b), flowing a flush medium through the acoustic chamber to flush the washed particles from the acoustic chamber.

In some examples, a standing wave generating assembly generates the standing wave within the standing wave volume when activated and terminates generation of the standing wave when inactivated, and the method further includes, after step (a) and prior to step (b), inactivating the standing wave generating assembly to facilitate settling of the raw particle concentrate within the acoustic chamber.

In some examples, a standing wave generating assembly generates the standing wave within the standing wave volume when activated and terminates generation of the standing wave when inactivated, and the method further includes, after step (b), inactivating the standing wave generating assembly to facilitate settling of the washed particles within the acoustic chamber.

In some examples the method further includes injecting the washed particles into a human body.

According to some aspects, an acoustic chamber system for washing particles includes: (a) an acoustic chamber; (b) a standing wave generating assembly for generating a standing wave in a standing wave volume of the acoustic chamber; and (c) a fluid system including a suspension medium line for supplying a suspension of the particles in a suspension medium from a suspension medium reservoir, and a wash medium line for supplying a wash medium from a wash medium reservoir. The fluid system is configurable to: (i) a particle concentration condition in which the suspension medium line and the acoustic chamber are in fluid communication for supplying the suspension medium to the standing wave volume, and (ii) a wash condition in which the wash medium line and the acoustic chamber are in fluid communication for supplying the wash medium to a settling volume of the acoustic chamber, the settling volume below the standing wave volume.

In some examples, the wash medium line and the acoustic chamber are in fluid isolation from each other when the fluid system is in the particle concentration condition.

In some examples, the suspension medium line and the acoustic chamber are in fluid isolation from each other when the fluid system is in the wash condition.

In some examples, the acoustic chamber includes a bottom port below the settling volume. The bottom port provides fluid communication between the wash medium line and the settling volume when the fluid system is in the wash condition.

In some examples, the bottom port provides fluid communication between the suspension medium line and the settling volume when the fluid system is in the particle concentration condition.

In some examples, the acoustic chamber includes a side port above the settling volume. The side port provides fluid communication between the suspension medium line and the acoustic chamber when the fluid system is in the particle concentration condition. In some examples, the side port is below the standing wave volume.

In some examples, the fluid system is configurable to a combined condition in which the suspension medium line and the acoustic chamber are in fluid communication for supplying the suspension medium to the standing wave volume, and at the same time the wash medium line and the acoustic chamber are in fluid communication for supplying the wash medium to the settling volume.

According to some aspects, an acoustic chamber apparatus for washing particles includes: an acoustic chamber including a chamber bottom portion defining a settling volume for accumulating a particle concentrate of the particles. The chamber bottom portion has a first bottom port below the settling volume and at least one second bottom port spaced apart from the first bottom port. The first and second bottom ports are for directing flow of a wash medium into the settling volume. The acoustic chamber further includes a chamber top portion having a top port for evacuating the wash medium from the acoustic chamber. The acoustic chamber apparatus further includes a standing wave generating assembly for generating a standing wave in a standing wave volume of the acoustic chamber. The standing wave volume is above the settling volume.

In some examples, the first bottom port is configured to direct flow of the wash medium into the settling volume in a first direction, and the second bottom port is configured to direct flow of the wash medium into the settling volume in a second direction different from the first direction.

In some examples, the chamber bottom portion includes a bottom end of the acoustic chamber and a side wall extending upwardly from the bottom end. The bottom end includes the first bottom port and the side wall includes the second bottom port.

In some examples, the acoustic chamber further includes a side port above the settling volume. The side port is configured to direct flow of a suspension of the particles in a suspension medium into the acoustic chamber for supplying the suspension medium to the standing wave volume. In some examples, the side port is below the standing wave volume.

According to some aspects, a method of washing biological particles, such as cells, in an acoustic chamber includes: (a) flowing a suspension of the biological particles in a suspension medium from a first bioreactor through a standing wave generated in a standing wave volume of the acoustic chamber to retain within the acoustic chamber at least some of the biological particles as raw particle concentrate; (b) after step (a), flushing the raw particle concentrate from the acoustic chamber and back to the first bioreactor, and filling the first bioreactor with a first growth medium; (c) after step (b), repeating step (a); (d) after step (c), flowing a wash medium through the acoustic chamber to wash within the acoustic chamber at least some of the particles of the raw particle concentrate, and retaining within the acoustic chamber at least some washed particles; and (e) after step (d), flushing the washed particles from the acoustic chamber.

In some examples, the method further includes filling a second bioreactor with a second growth medium, and wherein during step (e) the washed particles are flushed from the acoustic chamber into the second bioreactor.

In some examples, step c) includes repeating step a) several times, and repeating step b) prior to each repetition of step a).

BRIEF DESCRIPTION OF THE DRAWINGS

The drawings included herewith are for illustrating various examples of methods, systems, and apparatuses of the present specification and are not intended to limit the scope of what is taught in any way. In the drawings.

DETAILED DESCRIPTION

Figure 1:
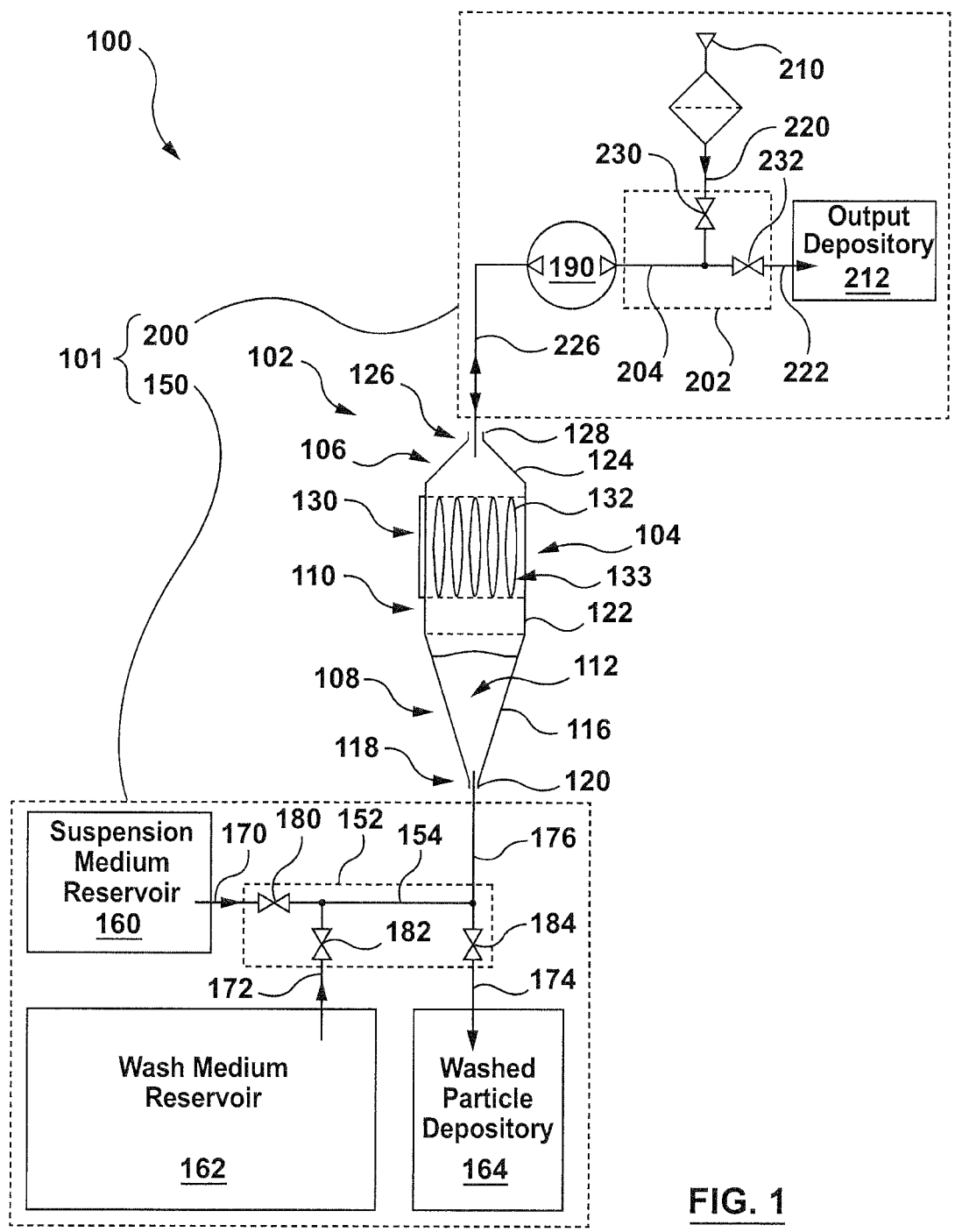
FIG. 1 is a schematic view of an example acoustic chamber system for washing particles.

Various apparatuses, systems, or methods will be described below to provide an example of an embodiment of the claimed subject matter. No embodiment described below limits any claim and any claim may cover apparatuses, systems, or methods that differ from those described below. The claims are not limited to apparatuses, systems, or methods having all of the features of any one apparatus, system, or method described below or to features common to multiple or all of the apparatuses, systems, and methods described below. It is possible that an apparatus, system, or method described below is not an embodiment of any claim. Any invention disclosed in an apparatus, system, or method described below that is not claimed in this document may be the subject matter of another protective instrument, for example, a continuing patent application, and the applicants, inventors or owners do not intend to abandon, disclaim or dedicate to the public any subject matter by its disclosure in this document.

Various applications require concentrating particles that are suspended in a suspension medium. In bioreactor applications, for example, it is often desirable to concentrate biological particles suspended in a suspension medium, so that the biological particles can be harvested and/or used in a bioreactor culture process. The biological particles may be, for example, cells, cell aggregates, micro-carriers, and/or combinations thereof. In biomedical applications, it may be desirable to concentrate biological particles such as, for example, cells suspended in a suspension medium supplied from a human body. While the above examples are directed to biological particles, the present teachings are applicable to other types of particles suspended in a suspension medium.

In some examples, particles of a selected size can be concentrated using an acoustic chamber. The acoustic chamber can include an acoustically active standing wave volume in which an acoustic standing wave is generated. The standing wave can be generated to have a wavelength corresponding to the selected size of particles to be retained and concentrated within the acoustic chamber. The suspension of particles in the suspension medium can be supplied to the acoustic chamber. As the suspension medium flows through the standing wave volume, induced ultrasonic forces within the standing wave volume can move suspended particles of the selected size toward antinodal areas of the standing wave. The suspended particles can migrate into the antinodal areas and form particle aggregates, and the particle aggregates can be retained within the acoustic chamber via the standing wave.

The particle-depleted suspension medium and other components within the suspension medium having a size not corresponding to the wavelength of the standing wave can flow through the standing wave volume and out from the acoustic chamber. When the particle aggregates become sufficiently large, the particle aggregates may settle under the force of gravity into an acoustically inactive settling volume of the chamber below the standing wave volume. The settling particles can accumulate in the settling volume as particle concentrate. As used herein, the term "particle concentrate" includes particles and/or particle aggregates retained within the acoustic chamber (e.g. in the standing wave volume), and/or settled or settling particles accumulated within the settling volume.

In some examples, it may be desirable to wash the particles of the particle concentrate prior to harvesting the particles and/or using the particles in a subsequent application. For example, it may be desirable to wash the particles of the particle concentrate clean or partially clean of the suspension medium and/or other contaminants such as cell growth, enzymes, proteins, or the like, so that the washed particles can be harvested, or used in a bioreactor culture process, or injected into a human body, or frozen for later use. In some examples, the suspension medium may comprise a freezing medium for facilitating freezing of the particles. In some examples, the frozen particles may be thawed and washed clean of the freezing medium prior to use of the particles in a subsequent application. This may be desirable in examples in which the freezing medium is, for example, toxic.

The present specification relates to systems, methods, and apparatuses in which particles of the particle concentrate may be washed directly within the acoustic chamber. A wash medium may be supplied directly to the acoustic chamber from a wash medium reservoir to wash the particles of the particle concentrate while the particle concentrate is retained within the chamber.

Referring to FIG. 1, an example acoustic chamber system 100 for washing particles is illustrated. The acoustic chamber system 100 includes an acoustic chamber apparatus 102 for washing particles. In the example illustrated, the acoustic chamber apparatus 102 includes a chamber 104 (also referred to as an acoustic chamber 104), and a standing wave generating assembly 130 for generating a standing wave 132 in a standing wave volume 133 of the chamber 104. The chamber 104 includes a chamber top portion 106, an opposed chamber bottom portion 108, and a chamber central portion 110 extending between the chamber top and bottom portions 106, 108. In the example illustrated, the chamber bottom portion 108 defines a settling volume 112 for accumulating particle concentrate.

In the example illustrated, the chamber bottom portion 108 has a bottom portion sidewall 116 tapering downwardly toward a bottom end 118 of the chamber 104. In the example illustrated, the bottom portion sidewall 116 is generally conical. In the example illustrated, the chamber 104 includes a bottom port 120 at the bottom end 118 below the settling volume 112. In the example illustrated, the bottom port 120 is configured to conduct fluid to and/or from the settling volume 112. The chamber central portion 110 has a central portion sidewall 122 extending from the chamber bottom portion 108 to the chamber top portion 106. In the example illustrated, the chamber top portion 106 further has a top portion sidewall 124 tapering upwardly toward a top end 126 of the chamber 104. In the example illustrated, the chamber top portion 106 is generally conical. In the example illustrated, the chamber 104 includes a top port 128 at the top end 126.

In the example illustrated, the standing wave generating assembly 130 generates the standing wave 132 in the standing wave volume 133 of the chamber 104 when activated. The standing wave volume 133 is referred to herein as an "active" standing wave volume 133 when the standing wave generating assembly 130 is activated. When inactivated, the standing wave generating assembly 130 terminates generation of the standing wave 132. In the example illustrated, the standing wave volume 133 is above the settling volume 112. In the example illustrated, the standing wave volume 133 is in an upper portion of the chamber central portion 110. In alternative examples, the standing wave volume 133 can be in another portion of the chamber 104.

Figure 2:
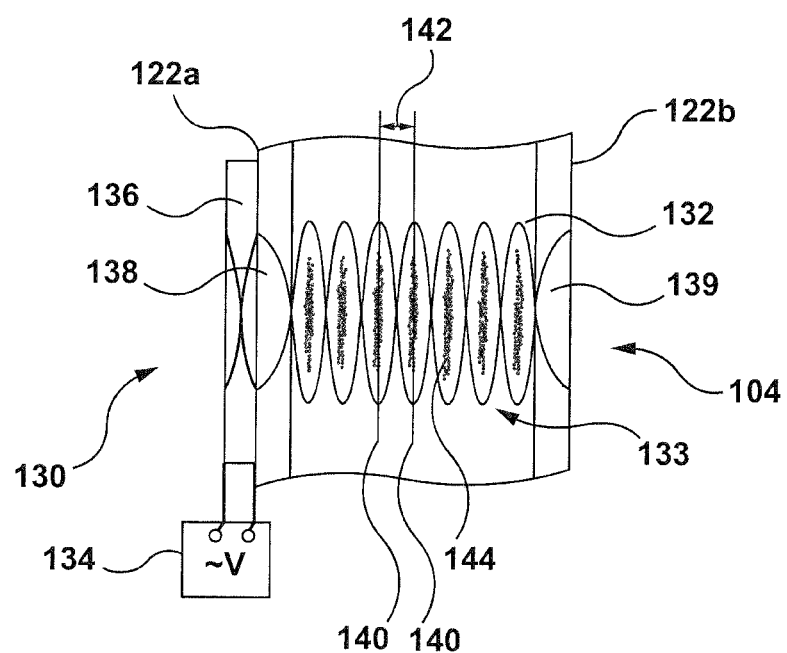
FIG. 2 is a schematic view of a standing wave generated in a standing wave volume of an acoustic chamber of the acoustic chamber system of FIG. 1.

Referring to FIG. 2, in the example illustrated, the standing wave generating assembly 130 includes a standing wave signal generator 134 coupled to an ultrasonic transducer plate 136. The ultrasonic transducer plate 136 may include piezoelectric, magnetostrictive, or mechanically or otherwise excitable layers for emitting acoustic energy. In the example illustrated, the transducer plate 136 includes a piezoelectric layer formed of a polarized lead-zirconium-titanate plate, with both sides of the piezoelectric layer covered at least in part by a thin metal electrode layer.

The transducer plate 136 can be integrated into, or bonded from the outside onto, a sidewall of the chamber 104 defining the standing wave volume 133 to provide a transducing wall 138. In the example illustrated, the transducer plate 136 is bonded from the outside onto one side 122a of an upper portion of the central portion sidewall 122. An opposed side 122b of the central portion sidewall 122 oriented parallel to the transducing wall 138 acts as an acoustic reflecting wall 139.

In the example illustrated, the standing wave signal generator 134 is configured to drive the transducer plate 136 to emit ultrasonic waves through the standing wave volume 133 of the chamber 104 toward the reflecting wall 139. The reflecting wall 139 reflects the emitted ultrasonic waves back toward the transducing wall 138. Superposition of the emitted and reflected ultrasonic waves forms the standing wave 132 within the standing wave volume 133. The standing wave 132 is characterized by a static pattern of areas of maximum acoustic displacement of the standing wave (i.e., antinodal areas 140) oriented parallel to the transducing and reflecting walls 138, 139 of the chamber 104.

The transducing and reflecting walls 122a, 122b of the chamber 104 can be formed of acoustically non-absorbing materials. Suitable materials may include, but are not limited to, glass, metals, ceramic, and/or combinations thereof. Alternatively, the transducing and reflecting walls 122a, 122b may be formed of thin plastic layers. To minimize acoustic energy loss, the thickness of the thin plastic layers forming the transducing and reflecting walls 122a, 122b can be less than the wavelength of a standing wave generated in the chamber 104. The remaining portions of the chamber 104 can be formed of the same material as the transducing and reflecting walls 122a, 122b. Alternatively, the remaining portions of the chamber 104 may be formed of a material different than that of the transducing and reflecting walls 122a, 122b.

The standing wave signal generator 134 can be configured to provide an ultrasonic frequency of the standing wave 132 ranging from 100 kHz to 10 MHz. The ultrasonic frequency can be selected based on the diameter of the particles to be concentrated within the acoustic chamber. In some examples, the ultrasonic frequency can be selected to provide an antinode to antinode distance 142 (equal to half the wave length of the standing wave 132) of approximately 10 to 100 times the typical diameter of the particles to be concentrated. In other examples, the ultrasonic frequency can be selected to provide an antinode to antinode distance 142 of approximately 15 to 50 times the typical diameter of the particles to be concentrated.

Referring back to FIG. 1, in the example illustrated, the acoustic chamber system 100 further includes a fluid system 101 for directing and regulating fluid flow through the chamber 104. In the example illustrated, the fluid system 101 includes a first sub-system 150 in fluid communication with a second sub-system 200 via the chamber 104.

In the example illustrated, the first sub-system 150 includes a suspension medium reservoir 160, a wash medium reservoir 162, and a washed-particle depository 164. The suspension medium reservoir 160 can store a suspension of the particles in a suspension medium. The wash medium reservoir 162 can store a wash medium for washing the particles. The washed-particle depository 164 can be used for depositing washed particles.

In the example illustrated the first sub-system 150 further includes a suspension medium line 170 for supplying the suspension medium from the suspension medium reservoir 160, a wash medium line 172 for supplying the wash medium from the wash medium reservoir, a washed-particle line 174 for depositing washed particles into the washed-particle depository 164, and a bottom port line 176.

In the example illustrated, the first sub-system 150 further includes a first fluid manifold 152 for directing and regulating fluid communication between the chamber 104 and the suspension medium reservoir 160, the wash medium reservoir 162, and the washed-particle depository 164. The first fluid manifold 152 includes a first header 154. The bottom port line 176 is coupled to the bottom port 120 of the chamber 104 and can provide fluid communication between the settling volume 112 of the chamber 104 and the first header 154 via the bottom port 120. The suspension medium line 170 can provide fluid communication between the suspension medium reservoir 160 and the first header 154. The wash medium line 172 can provide fluid communication between the wash medium reservoir 162 and the first header 154. The washed-particle line 174 can provide fluid communication between the washed-particle depository 164 and the first header 154.

In the example illustrated, the first manifold 152 includes a suspension medium valve 180 coupling the suspension medium line 170 to the first header 154, a wash medium valve 182 coupling the wash medium line 172 to the first header 154, and a washed-particle valve 184 coupling the washed-particle line 174 to the first header 154.

In the example illustrated, the suspension medium valve 180 is movable between an open position in which the suspension medium line 170 is in fluid communication with the first header 154, and a closed position in which the suspension medium line 170 is in fluid isolation from the first header 154. The wash medium valve 182 is movable between an open position in which the wash medium line 172 is in fluid communication with the first header 154, and a closed position in which the wash medium line 172 is in fluid isolation from the first header 154. The washed-particle valve 184 is movable between an open position in which the washed-particle line 174 is in fluid communication with the first header 154, and a closed position in which the washed-particle line 174 is in fluid isolation from the first header 154.

In the example illustrated, the second sub-system 200 includes a flush medium supply 210 and an output depository 212. The flush medium supply 210 can supply a flush medium. In the example illustrated, the flush medium is air. In alternative examples, the flush medium can be or include the wash medium, or a different medium. The output depository 212 can be used for depositing fluid drawn through the chamber 104 from the first sub-system 150.

In the example illustrated, the second sub-system 200 further includes a flush medium line 220 for supplying the flush medium from the flush medium supply 210, an output line 222 for depositing fluid into the output depository 212, and a top port line 226.

In the example illustrated, the second sub-system 200 further includes a second fluid manifold 202 for directing and regulating fluid communication between the chamber 104 and the flush medium supply 210 and the output depository 212. The second fluid manifold 202 includes a second header 204. The top port line 226 is coupled to the top port 128 of the chamber 104 and can provide fluid communication between the chamber 104 and the second header 204. The flush medium line 220 can provide fluid communication between the flush medium supply 210 and the second header 204. The output line 222 can provide fluid communication between the output depository 212 and the second header 204.

In the example illustrated, the second manifold 202 includes a flush medium valve 230 coupling the flush medium line 220 to the second header 204, and an output valve 232 coupling the output line 222 to the second header 204. In the example illustrated, the flush medium valve 230 is movable between an open position in which the flush medium line 220 is in fluid communication with the second header 204, and a closed position in which the flush medium line 220 is in fluid isolation from the second header 204. The output valve 232 is movable between an open position in which the output line 222 is in fluid communication with the second header 204, and a closed position in which the output line 222 is in fluid isolation from the second header 204.

In the example illustrated, the fluid system 101 further includes a fluid pump 190 for conducting fluid through the first sub-system 150, the chamber 104, and the second sub-system 200. In the example illustrated, the second sub-system 200 includes the pump 190, and the pump 190 is positioned between the top port line 226 and the second manifold 204. In the example illustrated, the pump 190 is operable in a pump forward direction and a pump reverse direction. In the pump forward direction, fluid is conducted in a fluid forward direction. In the fluid forward direction the fluid is conducted from the first sub-system 150 to the second sub-system 200 via the chamber 104. In the pump reverse direction, fluid is conducted in a fluid reverse direction. In the fluid reverse direction, the fluid is conducted from the second sub-system 200 to the first sub-system 150 via the chamber 104.

In the example illustrated, the fluid pump 190 includes a bi-directional pump for conducting the fluid in the fluid forward and fluid reverse directions. The bi-directional pump can conduct fluid from the first sub-system 150 to the output depository 212 when the pump 190 is operated in the pump forward direction. The bi-directional pump can conduct flush medium from the flush medium supply 210 to the first sub-system 150 when the pump 190 is operated in the pump reverse direction.

In alternative examples, the fluid pump 190 can include a forward-direction pump and a reverse-direction pump. The forward- and reverse-direction pumps can be positioned in the same one of the sub-systems 150, 200. Alternatively, the forward-direction pump can be positioned in one of the sub-systems 150, 200, and the reverse-direction pump can be positioned in the other one of the sub-systems 150, 200.

When the fluid pump 190 is operated in the pump forward direction, the forward-direction pump can conduct fluid in the fluid forward direction. The forward-direction pump can conduct fluid from the first sub-system 150 to the output depository 212 via the chamber 104 when the fluid pump 190 is operated in the pump forward direction. In some examples, the output depository line 222 can include the forward-direction pump. In such an example, output valve 232 can be omitted.

When the fluid pump 190 is operated in the pump reverse direction, the reverse-direction pump can conduct fluid in the fluid reverse direction. In some examples, the reverse-direction pump can conduct flush medium from the flush medium supply 210 to the first sub-system 150 via the chamber 104 when the fluid pump 190 is operated in the pump reverse direction. In some examples, the flush medium line 220 can include the reverse-direction pump. In such an example, flush medium valve 230 can be omitted.

In alternative examples, the reverse-direction pump can be omitted, and the fluid can be conducted in the fluid reverse direction under the force of gravity, or pressurized air.

In the example illustrated, the fluid system 101 is configurable to a particle concentration condition, a wash condition, and a harvest condition.

In the particle concentration condition, the suspension medium line 170 and the chamber 104 are in fluid communication with each other for supplying the suspension medium to the standing wave volume 133. In the particle concentration condition, the pump 190 is operated in the pump forward direction, and the suspension medium valve 180 and the output valve 232 are in the open position. The bottom port 120 provides fluid communication between the suspension medium line 170 and the settling volume 112 when the fluid system 101 is in the particle concentration condition. In the example illustrated, the remaining valves are in the closed position when the fluid system 101 is in the particle concentration condition. In the example illustrated, the wash medium line 172 and the settling volume 112 are in fluid isolation from each other when the fluid system 101 is in the particle concentration condition.

In the wash condition, the wash medium line 172 and the settling volume 112 are in fluid communication with each other for supplying the wash medium to the settling volume 112. In the wash condition, the pump 190 is operated in the pump forward direction, and the wash medium valve 182 and the output valve 232 are in the open position. The bottom port 120 provides fluid communication between the wash medium line 172 and the settling volume 112 when the fluid system 101 is in the wash condition. In the example illustrated, the remaining valves are in the closed position when the fluid system 101 is in the wash condition. In the example illustrated, the suspension medium line 170 and the chamber 104 are in fluid isolation from each other when the fluid system 101 is in the wash condition.

In the harvest condition, the pump 190 is operated in the pump reverse direction; the washed-particle valve 184 and the flush medium valve 230 are in the open position; and the remaining valves are in the closed position. In the harvest condition, both the suspension medium line 170 and the wash medium line 172 are in fluid isolation from the chamber 104.

Figure 3:
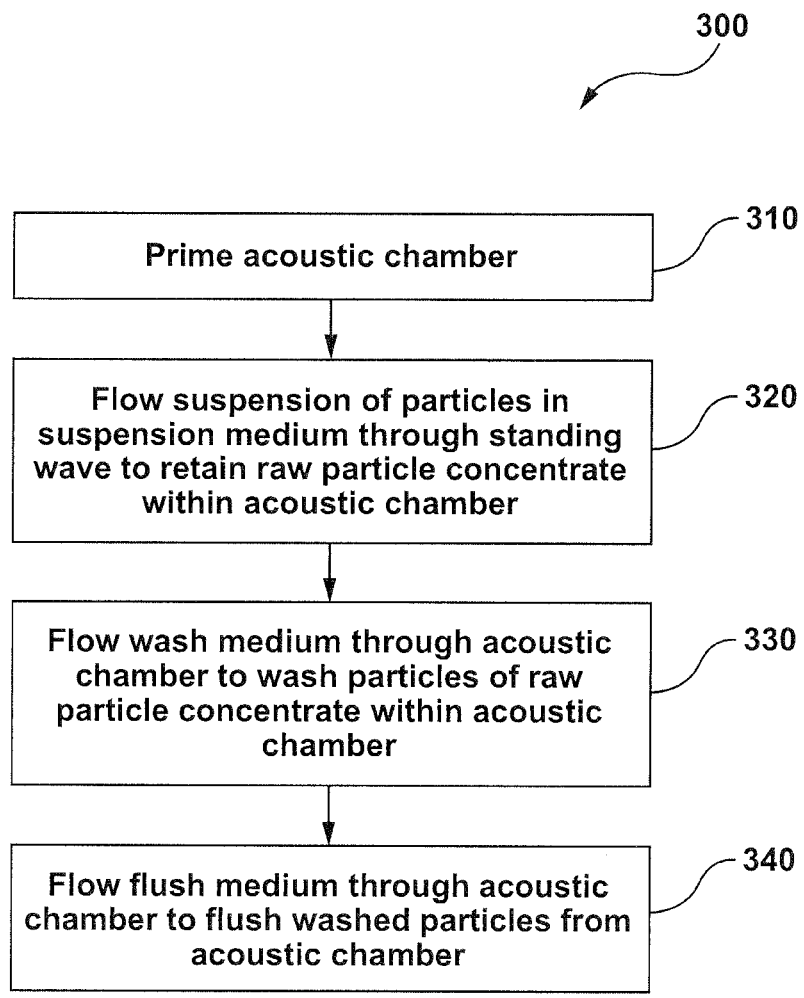
FIG. 3 is a flow chart illustrating an example particle washing method using the acoustic chamber system of FIG. 1.

Referring to FIG. 3, an example particle washing method 300 will be described. The particle washing method 300 will be described with reference to the acoustic chamber system 100. In alternative examples, the particle washing method 300 may be carried out using other acoustic chamber systems, and the acoustic chamber system 100 may be used according to other methods.

At step 310, the chamber 104 can be primed with a medium. In the example illustrated, the chamber 104 is primed with the suspension medium, the wash medium, or any other suitable medium to purge air from the chamber 104 and other components of the fluid system 101.

At step 320, the standing wave generating assembly 130 is activated to generate the standing wave 132 within the standing wave volume 133. The fluid system 101 is configured to the particle concentration condition to flow the suspension medium in the fluid forward direction from the suspension medium reservoir 160 through the chamber 104. In the particle concentration condition, the suspension of the particles in the suspension medium flows from the suspension medium reservoir 160 through the standing wave 132 within the active standing wave volume 133 to retain and accumulate within the chamber 104 at least some of the particles as raw particle concentrate.

Referring to FIG. 2, in the example illustrated, the pump 190 is configured to draw the suspension medium through the active standing wave volume 133 at a suspension medium flow rate that facilitates acoustically induced migration and aggregation of suspended particles into the antinodal areas 140 of the standing wave 132. In the example illustrated, as the suspension of the particles in the suspension medium flows through the active standing wave volume 133, induced ultrasonic forces within the active standing wave volume 133 move the suspended particles toward the antinodal areas 140. As the suspended particles migrate into the antinodal areas 140, the suspended particles form raw particle aggregates 144.

In the example illustrated, the raw particle aggregates 144 are retained within the chamber 104 via the standing wave 132, while the particle-depleted suspension medium flows out from the chamber 104 to the output depository 212 through the top port 128. The raw particle aggregates accumulate as raw particle concentrate in the chamber 104, and some may settle within the settling volume 112. Flow of the suspension medium through the bottom port 120 may agitate any settling raw particle aggregates. This may, for example, facilitate loosening of the raw particle concentrate and may help inhibit formation of a too tightly packed or sticky pellet within the settling volume 112.

Referring back to FIG. 1, in the particle concentration condition, the suspension medium flows in the fluid forward direction from the suspension medium reservoir 160 to the output depository 212 through the suspension medium line 170, the first header 154, the bottom port line 176, the bottom port 120, the settling volume 112, the standing wave volume 133, the top port 128, the top port line 226, the second header 204, and the output line 222.

Optionally, after step 320 and prior to step 330, the pump 190 can be stopped and the standing wave generating assembly 130 can be inactivated to facilitate settling of the raw particle concentrate within the chamber 104. In some examples, once the raw particle concentrate settles within the chamber 104 (for example, within the settling volume 112), step 320 can optionally be repeated to accumulate additional particles within the chamber 104. In some examples, the standing wave generating assembly 130 can be inactivated and reactivated one or more times during step 320 to facilitate settling of the raw particle concentrate.

Once a desired amount of the particles accumulates as raw particle concentrate within the chamber 104, the particle washing method 300 can proceed to step 330. At step 330, the fluid system 101 is configured to the wash condition to flow the wash medium in the fluid forward direction from the wash medium reservoir 162 through the chamber 104 to wash within the chamber 104 at least some of the particles of the raw particle concentrate. As the wash medium flows through the chamber 104 and the raw particle concentrate, at least some of the particles of the raw particle concentrate are washed clean or partially clean of the suspension medium and/or other contaminants.

In the example illustrated, at least some of the washed particles are retained within the acoustic chamber as washed particle concentrate. In some examples, the pump 190 can be configured to draw the wash medium through the raw particle concentrate at a wash medium flow rate that facilitates washing of the raw particle concentrate and retention of washed particles within the chamber 104. In some examples, the wash medium flow rate may be low enough not to resuspend in the wash medium the particles of the raw particle concentrate.

In some examples, flow of the wash medium through the raw particle concentrate may resuspend some of the particles of the raw particle concentrate in the wash medium. The standing wave generating assembly 130 may be activated at step 330 to generate the standing wave 132 if previously inactivated, and the wash medium and any resuspended particles may flow into the active standing wave volume 133. The pump 190 can be configured to draw the wash medium through the active standing wave volume 133 at a wash medium flow rate that facilitates acoustically induced migration and aggregation of any resuspended particles into the antinodal areas 140 (FIG. 2) of the standing wave 132. In the example illustrated, as any resuspended particles flow into the active standing wave volume 133, the resuspended particles form washed particle aggregates in the antinodal areas 140.

In the example illustrated, the washed particle aggregates can be retained within the chamber 104 via the standing wave 132, while the wash medium flows out from the chamber 104 to the output depository 212 through the top port 128. Flow of the wash medium past the suspended washed particle aggregates can further wash the suspension medium and/or other contaminants from the particles. The suspension medium and/or other contaminants can be carried off with the wash medium from the chamber 104 to the output depository 212 through the top port 128. The washed particle aggregates can accumulate within the chamber 104 as washed particle concentrate, and some may settle within the settling volume 112. Flow of the wash medium through the bottom port 120 may agitate any settling washed particle aggregates. This may, for example, facilitate loosening of the washed particle concentrate and may help inhibit formation of a too tightly packed or sticky pellet within the settling volume 112.

In the wash condition, the wash medium flows from the wash medium reservoir 162 to the output depository 212 through the wash medium line 172, the first header 154, the bottom port line 176, the bottom port 120, the settling volume 112, the raw particle concentrate, the standing wave volume 133, the top port 128, the top port line 226, the second header 204, and the output line 222.

Optionally, after step 330 and prior to step 340, the pump 190 can be stopped and the standing wave generating assembly 130 can be inactivated to facilitate settling of the washed particle concentrate within the chamber 104. In some examples, once the washed particle concentrate settles within the chamber 104 (for example, within the settling volume 112), step 330 can optionally be repeated to further wash the particles within the chamber 104. In some examples, the standing wave generating assembly 130 can be inactivated and reactivated one or more times during step 330 to facilitate settling of the washed particle concentrate.

Once the particles have been washed, the particle washing method 300 can proceed to step 340. At step 340, the standing wave generating assembly 130 is inactivated, and the fluid system 101 is configured to the harvest condition to flush the washed particle concentrate from the chamber 104.

In the harvest condition, the flush medium flows in the fluid reverse direction through the chamber 104 from the flush medium supply 210. In the example illustrated, the pump 190 conducts the flush medium in the fluid reverse direction. In alternative examples, the flush medium can be conducted in the fluid reverse direction under the force of gravity. In the example illustrated, the flush medium flows from the flush medium supply 210 to the washed-particle depository 164 through the flush medium line 220, the second header 204, the top port line 226, the top port 128, and the settling volume 112 to flush the washed particle concentrate through the bottom port 120, the bottom port line 176, the first header 154, the washed-particle line 174, and into the washed-particle depository 164.

In alternative examples, the washed particle concentrate can be flushed from the chamber 104 by flowing fluid from the output depository 212 through the chamber 104 and into the washed-particle depository 164. In some examples, the fluid from the output depository 212 may be the wash medium. The fluid from the output depository 212 can be conducted in the fluid reverse direction by the pump 190, or alternatively, under the force of gravity or pressurized air. In such examples, the flush medium supply 210, the flush medium line 220, and the flush medium valve 230 may be omitted, and the output line 222 may include the pump 190.

In alternative examples, the washed particle concentrate can be flushed from the chamber 104 by releasing compressed air through the chamber 104 from a compressed air tank in fluid communication with the top port line 226. The flush medium supply 210, the flush medium line 220, and the flush medium valve 230 may be omitted in such examples.

Optionally, after step 340, steps 330 and 340 can be repeated to flush the chamber 104 with the wash medium to recover any remaining particles attached to the inner walls of the chamber 104.

Once the washed particle concentrate is flushed from the chamber 104, the pump 190 can be stopped and all the valves can be closed. In some examples, the particle washing method 300 can then be repeated. Once a sufficient amount of washed particles is collected in the washed-particle depository 164, the washed particle depository 164 can be sealed and removed from the acoustic chamber system 100, and can be replaced with a new washed-particle depository 164 for use in a subsequent cycle of the particle washing method 300.

Figure 4:
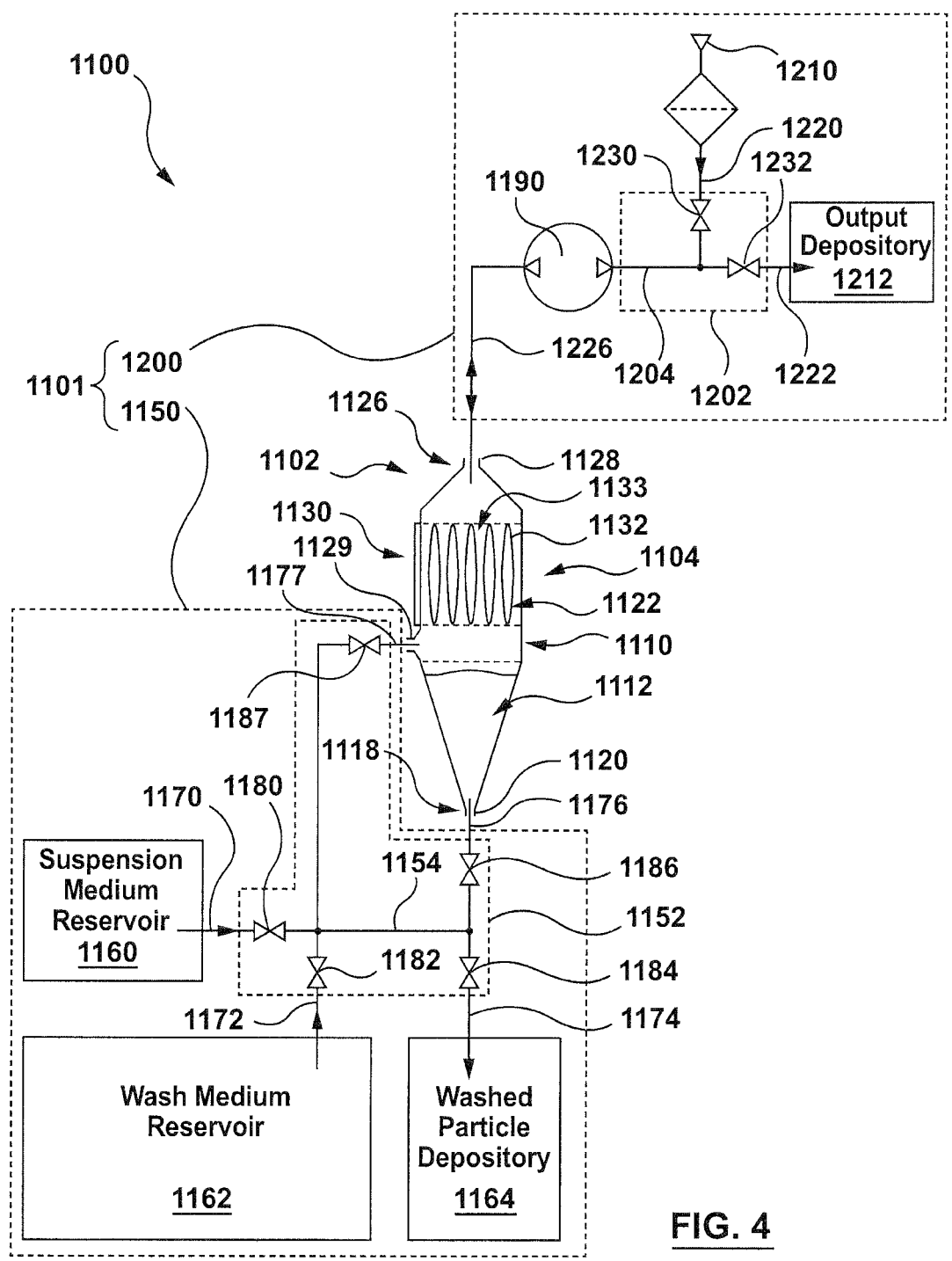
FIG. 4 is a schematic view of an alternative example acoustic chamber system for washing particles.

Referring to FIG. 4, an alternative example acoustic chamber system 1100 is illustrated. The acoustic chamber system 1100 has similarities to the acoustic chamber system 100, and like features are identified by like reference characters, incremented by 1000.

In the example illustrated, the acoustic chamber system 1100 includes an acoustic chamber apparatus 1102. The acoustic chamber apparatus 1102 includes a chamber 1104 and a standing wave generating assembly 1130 for generating a standing wave 1132 in a standing wave volume 1133 of the chamber 1104. The standing wave volume 1133 is above a settling volume 1112 of the chamber 1104. In the example illustrated, the standing wave volume 1133 is in an upper portion of the chamber central portion 1110.

In the example illustrated, the chamber 1104 includes a bottom port 1120 below the settling volume 1112 at a bottom end 1118 of the chamber 1104, and a top port 1128 at a top end 1126 of the chamber 1104. In the example illustrated, the chamber 1104 further includes a side port 1129 for conducting fluid to and/or from the chamber 1104. In the example illustrated, the side port 1129 is above the settling volume 1112. In the example illustrated, the side port 1129 is below the standing wave volume 1133. In the example illustrated, the side port 1129 is at a lower portion of a central portion sidewall 1122 of the chamber 1104. In the example illustrated, the side port 1129 can conduct fluid into and/or out from an intermediate volume of the chamber 1104 below the standing wave volume 1133 and above the settling volume 1112. In the example illustrated, the side port 1129 is configured to conduct fluid into the chamber 1104 in a horizontal first direction generally perpendicular to the acoustic antinodal planes of the standing wave 1132 (e.g., from left to right in FIG. 4).

In some examples, the side port 1129 can be at a location different from that shown in FIG. 4. For example, the side port 1129 can be located and configured to conduct fluid directly to and/or from the standing wave volume 1133. In some examples, the side port 1129 can be configured to conduct fluid into the chamber 1104 in a direction different from that shown in FIG. 4. For example, the side port 1129 can be configured to conduct fluid into the chamber 1104 in a horizontal second direction generally parallel to the acoustic antinodal planes of the standing wave 1132 (e.g., into the page in FIG. 4). In some examples, the side port 1129 can be configured to conduct fluid into the chamber 1104 in a direction generally oblique to the first direction, the second direction, and/or the acoustic antinodal planes of the standing wave 1132. In some examples, the side port 1129 can be configured to conduct fluid into the chamber 1104 in a generally vertical direction. In some examples, two or more side ports 1129 can be included, with each side port 1129 configured to conduct fluid into the chamber 1104 in a respective direction.

In the example illustrated, the acoustic chamber system 1100 further includes a fluid system 1101. The fluid system 1101 includes a first sub-system 1150 in fluid communication with a second sub-system 1200 via the chamber 1104.

In the example illustrated, the first sub-system 1150 includes a suspension medium reservoir 1160, a wash medium reservoir 1162, and a washed-particle depository 1164. In the example illustrated, the first sub-system 1150 further includes a suspension medium line 1170, a wash medium line 1172, a washed-particle line 1174, a bottom port line 1176, and a side port line 1177.

In the example illustrated, the first sub-system 1150 further includes a first fluid manifold 1152 having a first header 1154. The side port line 1177 is coupled to the side port 1129 of the chamber 1104 and can provide fluid communication between the first header 1154 and the chamber 1104 via the side port 1129. In the example illustrated, the first manifold 1152 includes a suspension medium valve 1180, a wash medium valve 1182, a washed-particle valve 1184, a bottom port valve 1186 coupling the bottom port line 1176 to the first header 1154, and a side port valve 1187 coupling the side port line 1177 to the first header 1154.

In the example illustrated, the bottom port valve 1186 is movable between an open position in which the bottom port line 1176 is in fluid communication with the first header 1154, and a closed position in which the bottom port line 1176 is in fluid isolation from the first header 1154. The side port valve 1187 is movable between an open position in which the side port line 1177 is in fluid communication with the first header 1154, and a closed position in which the side port line 1177 is in fluid isolation from the first header 1154.

In the example illustrated, the second sub-system 1200 includes a flush medium supply 1210 and an output depository 1212. In the example illustrated, the second sub-system 1200 includes a second fluid manifold 1202, a flush medium line 1220, an output line 1222, a top port line 1226, and a fluid pump 1190. In the example illustrated, the second manifold 1202 includes a second header 1204, a flush medium valve 1230, and an output valve 1232.

In the example illustrated, the fluid system 1101 is configurable to a particle concentration condition, an evacuation condition, a fill condition, a wash condition, and a harvest condition.

In the particle concentration condition, the suspension medium line 1170 and the chamber 1104 are in fluid communication with each other for supplying the suspension medium to the standing wave volume 1133. In the particle concentration condition, the pump 1190 is operated in the pump forward direction, and the suspension medium valve 1180, the side port valve 1187, and the output valve 1232 are in the open position. In the example illustrated, the side port 1129 provides fluid communication between the suspension medium line 1170 and the chamber 1104 when the fluid system 1101 is in the particle concentration condition. In the example illustrated, the remaining valves are in the closed position when the fluid system 1101 is in the particle concentration condition. In the example illustrated, the wash medium line 1172 and the settling volume 1112 are in fluid isolation from each other when the fluid system 1101 is in the particle concentration condition.

In the evacuation condition, the pump 1190 is operated in the pump reverse direction; the suspension medium valve 1180, the side port valve 1187, and the flush medium valve 1230 are in the open position; and the remaining valves are in the closed position.

In the fill condition, the pump 1190 is operated in the pump forward direction; the wash medium valve 1182, the side port valve 1187, and the output valve 1232 are in the open position; and the remaining valves are in the closed position.

In the wash condition, the wash medium line 1172 and the settling volume 1112 are in fluid communication with each other for supplying the wash medium to the settling volume 1112. In the wash condition, the pump 1190 is operated in the pump forward direction, and the wash medium valve 1182, the bottom port valve 1186, and the output valve 1232 are in the open position. In the example illustrated, the bottom port 1120 provides fluid communication between the wash medium line 1172 and the settling volume 1112 when the fluid system 1101 is in the wash condition. In the example illustrated, the remaining valves are in the closed position when the fluid system 1101 is in the wash condition. In the example illustrated, the suspension medium line 1170 and the chamber 1104 are in fluid isolation from each other when the fluid system 1101 is in the wash condition.

In the harvest condition, the pump 1190 is in the pump reverse direction; the washed-particle valve 1184, the bottom port valve 1186, and the flush medium valve 1230 are in the open position; and the remaining valves are in the closed position.

Figure 5:
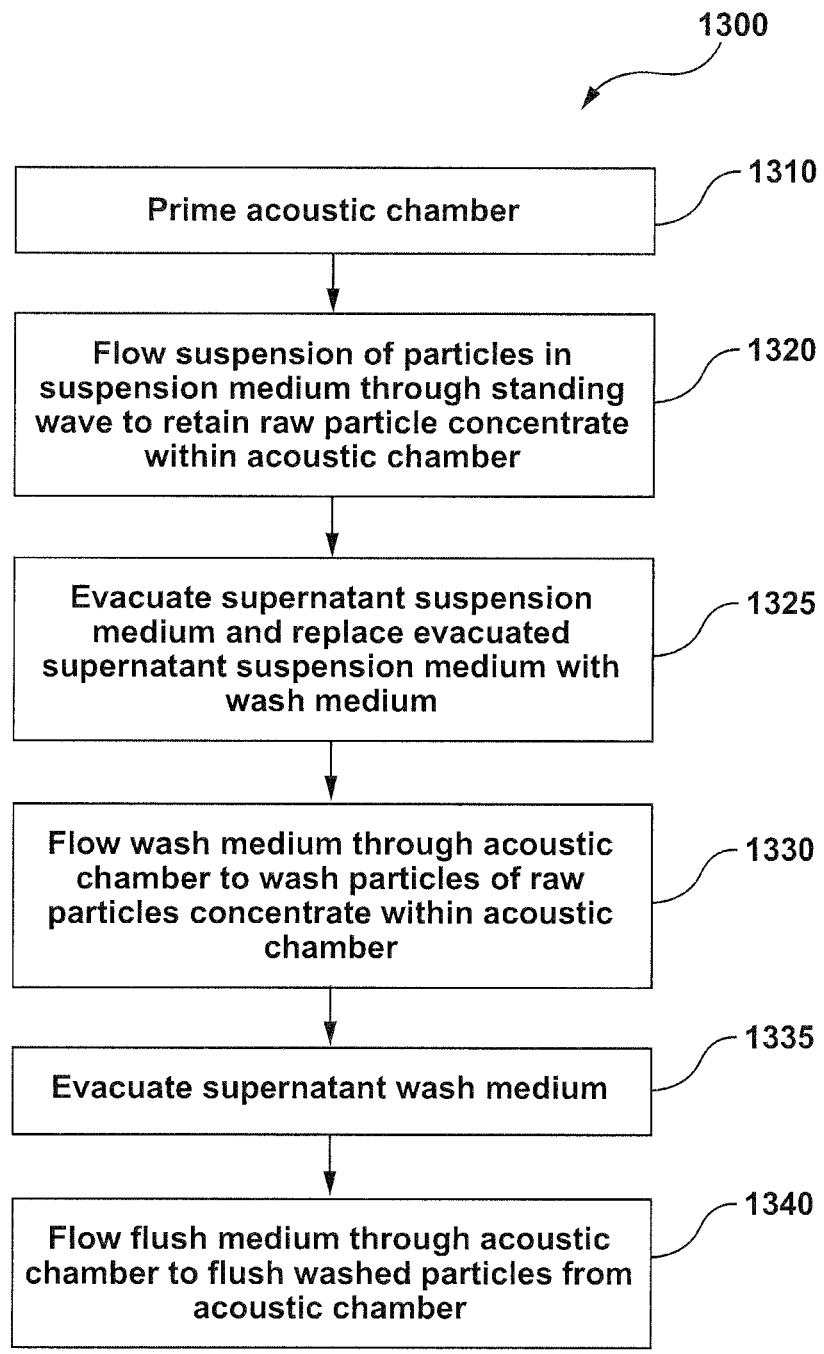
FIG. 5 is a flow chart illustrating an example particle washing method using the acoustic chamber system of FIG. 4.

Referring to FIG. 5, a particle washing method 1300 will be described. The particle washing method 1300 will be described with reference to the acoustic chamber system 1100. In alternative examples, the particle washing method 1300 may be carried out using other acoustic chamber systems, and the acoustic chamber system 1100 may be used according to other methods. The particle washing method 1300 has similarities to the particle washing method 300, and like steps are identified by like reference characters, incremented by 1000.

At step 1310, the chamber 1104 can be primed with a medium.

At step 1320, the standing wave generating assembly 1130 is activated, and the fluid system 1101 is configured to the particle concentration condition to flow the suspension medium in the fluid forward direction from the suspension medium reservoir 1160 through the chamber 1104. In the particle concentration condition, the suspension of the particles in the suspension medium flows through the standing wave 1132 to retain and accumulate within the chamber 1104 at least some of the particles as raw particle concentrate.

In the examples illustrated, the suspension medium is drawn through the active standing wave volume 1133 at a suspension medium flow rate that facilitates acoustically induced migration and aggregation of suspended particles into antinodal areas of the standing wave 1132. As the suspended particles migrate into antinodal areas of the standing wave 1132, the suspended particles form raw particle aggregates 1144.

In the example illustrated, the raw particle aggregates 1144 are retained within the chamber 1104 via the standing wave 1132, while the particle-depleted suspension medium flows out from the chamber 1104 to the output depository 1212 through the top port 1128. The raw particle aggregates accumulate within the chamber 1104 as raw particle concentrate. When the raw particle aggregates become sufficiently large, the raw particle aggregates may settle under the force of gravity within the settling volume 1112.

In the particle concentration condition, the suspension medium flows from the suspension medium reservoir 1160 to the output depository 1212 through the suspension medium line 1170, the first header 1154, the side port line 1177, the side port 1129, the standing wave volume 1133, the top port 1128, the top port line 1226, the second header 1204, and the output line 1222. Flowing the suspension medium through the side port 1129 can help reduce resuspension of the raw particle concentrate settling in the settling volume 1112. This may facilitate sedimentation of the raw particle concentrate within the settling volume 1112. This may also increase the amount of particles retained within the chamber 1104, may permit a higher suspension medium flow rate of the suspension medium through the chamber 1104, and may shorten cycle time of the particle washing method 1300.

Optionally, in some examples, the bottom port valve 1186 can be opened for a brief period during step 1320 to permit the suspension medium to flow into the chamber 1104 through the bottom port 1120. Briefly flowing the suspension medium through the bottom port 1120 during step 1320 may agitate the raw particle concentrate, may keep the raw particle concentrate loose, and/or may inhibit the raw particle concentrate from forming a too tightly packed or sticky pellet within the settling volume 1112. This may allow for a more thorough washing of the raw particle concentrate during step 1330. In some examples, the wash medium may be conducted for a brief period through the bottom port 1120 for this purpose. In some examples, the flow rate of the suspension medium or the wash medium through the bottom port 1120 may be increased briefly to facilitate agitation and/or loosening of the raw particle concentrate and to help inhibit formation of a too tightly packed or sticky pellet. In some examples, gas bubbles can be introduced into the suspension medium or the wash medium flowing through the bottom port 1120 to facilitate agitation and/or loosening of the raw particle concentrate and to help inhibit formation of a too tightly packed or sticky pellet. In some examples, the chamber 1104 may be mechanically agitated, tilted, and/or flipped to facilitate agitation and/or loosening of the raw particle concentrate and to help inhibit formation of a too tightly packed or sticky pellet.

In some examples, the raw particle concentrate pellet may be flushed from the chamber 1104 and then pushed back into the chamber 1104 to facilitate loosening of the raw particle concentrate. For example, the valves 1180 and 1186 may be opened and the pump 1190 may be operated in the pump reverse direction to flush the raw particle concentrate pellet through the bottom port 1120, the line 1176, and the header 1154. After a period of time, the pump 1190 may be operated in the pump forward direction to push the raw particle concentrate back into the chamber 1104 through the bottom port 1120 (and/or the side port 1129).

Once a desired amount of the particles accumulates as raw particle concentrate within the chamber 1104, the particle washing method 1300 can optionally proceed to step 1325. At step 1325, at least some of the supernatant suspension medium above the settling volume 1112 can be evacuated from the chamber 1104 while the raw particle concentrate is retained in the settling volume 1112 (in the form of raw particle sediment, for example), and the evacuated supernatant suspension medium can be replaced with the wash medium. Replacing at least some of the supernatant suspension medium with the wash medium can dilute the suspension medium in the chamber 1104, and may improve efficiency of the particle washing method 1300.

To evacuate the supernatant suspension medium, the fluid system 1101 is configured to the evacuation condition. In the evacuation condition, at least some of the supernatant suspension medium is evacuated from the chamber through the side port 1129 of the chamber 1104. In the evacuation condition, the flush medium flows from the flush medium supply 1210 to the suspension medium reservoir 1160 to flush some of the supernatant suspension medium from the chamber 1104 into the suspension medium reservoir 1160. The flush medium flows through the flush medium line 1220, the second header 1204, the top port line 1226, and the top port 1128 into the chamber 1104 to flush the supernatant suspension medium through the side port 1129, the side port line 1177, the first header 1154, the suspension medium line 1170, and into the suspension medium reservoir 1160.

Once a desired amount of supernatant suspension medium is evacuated, the fluid system 1101 can be configured to the fill condition to replace the evacuated supernatant suspension medium with the wash medium. In the fill condition, the wash medium flows from the wash medium reservoir 1162 into the chamber 1104 through the side port 1129. The wash medium flows through the wash medium line 1172, the first header 1154, the side port line 1177, the side port 1129, and into the chamber 1104 above the settling volume 1112 to replace the evacuated supernatant suspension medium.

Once a desired amount of the particles accumulate as raw particle concentrate in the chamber 1104, the particle washing method 1300 can proceed to step 1330. At step 1330, the fluid system 1101 is configured to the wash condition to flow the wash medium in the fluid forward direction from the wash medium reservoir 1162 through the chamber 1104 to wash within the chamber 1104 at least some of the particles of the raw particle concentrate. As the wash medium flows through the chamber 1104 and the raw particle concentrate, at least some of the particles of the raw particle concentrate are washed clean or partially clean of the suspension medium and/or other contaminants.

In the example illustrated, at least some of the washed particles are retained within the acoustic chamber as washed particle concentrate during step 1330. In some examples, the pump 1190 can be configured to draw the wash medium through the raw particle concentrate at a wash medium flow rate that facilitates washing of the raw particle concentrate and retention of the washed particles within the chamber 1104. In some examples, the wash medium flow rate may be low enough not to resuspend in the wash medium the particles of the raw particle concentrate.

In some examples, flow of the wash medium through the raw particle concentrate may resuspend some of the particles of the raw particle concentrate in the wash medium. The standing wave generating assembly 1130 may be activated at step 1330 to generate the standing wave 1132 if previously inactivated, and the wash medium and any resuspended particles may flow into the active standing wave volume 1133. In the example illustrated, as any resuspended particles flow into the active standing wave volume 1133, the particles form washed particle aggregates in antinodal areas of the standing wave 1132.

In the example illustrated, the washed particle aggregates can be retained within the chamber 1104 via the standing wave 1132, while the wash medium flows out from the chamber 1104 to the output depository 1212 through the top port 1128. Flow of the wash medium past the suspended washed particle aggregates can further wash the suspension medium and/or other contaminants from the particles. The suspension medium and/or other contaminants can be carried off with the wash medium from the chamber 1104 to the output depository 1212 through the top port 1128. The washed particle aggregates can accumulate within the chamber 1104 as washed particle concentrate. In the example illustrated, when the washed particle aggregates become sufficiently large, the washed particle aggregates may settle under the force of gravity within the settling volume 1112.

Optionally, in some examples, the flow rate of the wash medium through the bottom port 1120 may be increased briefly to facilitate agitation and/or loosening of the washed particle concentrate and to help inhibit formation of a too tightly packed or sticky pellet. In some examples, gas bubbles can be introduced into the wash medium flowing through the bottom port 1120 to facilitate agitation and/or loosening of the washed particle concentrate and to help inhibit formation of a too tightly packed or sticky pellet. In some examples, the chamber 1104 may be mechanically agitated, tilted, and/or flipped to facilitate agitation and/or loosening of the washed particle concentrate and to help inhibit formation of a too tightly packed or sticky pellet. In some examples, the washed particle concentrate pellet may be flushed from the chamber 1104 and then pushed back into the chamber 1104 to facilitate loosening of the washed particle concentrate.

In the wash condition, the wash medium flows from the wash medium reservoir 1162 to the output depository 1212 through the wash medium line 1172, the first header 1154, the bottom port line 1176, the bottom port 1120, the settling volume 1112, the raw particle concentrate, the standing wave volume 1133, the top port 1128, the top port line 1226, the second header 1204, and the output line 1222.

In some examples, steps 1320 and 1330 may be repeated prior to subsequent steps to alternately concentrate particles within the chamber 1104 and wash the concentrated particles within the chamber 1104.

After step 1330 and prior to step 1335, the fluid system 1101 can optionally be configured to the fill condition for a brief period. This optional step can draw the wash medium into the chamber 1104 through the side port 1129 to flush any particles within the side port line 1177 and the side port 1129 into the chamber 1104.

After step 1330 and prior to step 1340, the particle washing method can optionally proceed to step 1335. At step 1335, at least some of the supernatant wash medium above the settling volume 1112 is evacuated from the chamber 1104 while the washed particle concentrate is retained within the settling volume 1112 (in the form of washed particle sediment, for example). Evacuating at least some of the supernatant wash medium prior to step 1340 can increase the concentration of washed particles deposited into the washed-particle depository 1164 during subsequent steps.

To evacuate some of the supernatant wash medium, the fluid system 1101 is configured to the evacuation condition. In the evacuation condition, at least some of the supernatant wash medium is evacuated from the chamber through the side port 1129 of the chamber 1104. In the evacuation condition, the flush medium flows from the flush medium supply 1210 to the suspension medium reservoir 1160 to flush some of the wash medium from the chamber 1104 into the suspension medium reservoir 1160. In the example illustrated, the flush medium flows through the flush medium line 1220, the second header 1204, the top port line 1226, and the top port 1128 into the chamber 1104 to flush the supernatant wash medium through the side port 1129, the side port line 1177, the first header 1154, the suspension medium line 1170, and into the suspension medium reservoir 1160.

At step 1340, the standing wave generating assembly 1130 is inactivated, and the fluid system 1101 is configured to the harvest condition. In the harvest condition, the flush medium flows from the flush medium supply 1210 to the washed-particle depository 1164 through the flush medium line 1220, the second header 1204, the top port line 1226, the top port 1128, and the settling volume 1112 to flush the washed particle concentrate through the bottom port 1120, the bottom port line 1176, the first header 1154, the washed-particle line 1174, and into the washed-particle depository 1164.

In some examples, the acoustic chamber system may be configured so that the particle concentration step (step 1320 in FIG. 5) and the wash step (step 1330 in FIG. 5) occur simultaneously for at least a period of time. For example, in some examples the fluid system can be configurable to a combined condition in which the suspension medium line and the acoustic chamber are in fluid communication for supplying the suspension medium to the standing wave volume, and at the same time the wash medium line and the acoustic chamber are in fluid communication for supplying the wash medium to the settling volume of the acoustic chamber. For example, referring to FIG. 4, the suspension medium can flow through the side port 1129 to accumulate raw particle concentrate within the chamber 1104, and at the same time, the wash medium can flow through the bottom port 1120 to wash particles of the raw particle concentrate that settle within the settling volume 1112. In such examples, the fluid system 1101 can be configured to include a suspension medium pump for conducting the suspension medium through the side port 1129 at a suspension medium flow rate, and/or a wash medium pump for conducting the wash medium through the bottom port 1120 at a wash medium flow rate. In such examples, the first sub-system 1150 can be configured so that the suspension medium line 1170 and the side port feed line 1177 are in fluid communication with each other and in fluid isolation from the first header 1154 when the suspension medium valve 1180 is in the open position. The side port valve 1187 may be omitted in such examples. The suspension medium line 1170 can include the suspension medium pump, and/or the wash medium line 1182 can include the wash medium pump. The suspension medium pump and/or the wash medium pump may be provided in addition to or in lieu of the pump 1190.

Figure 6:
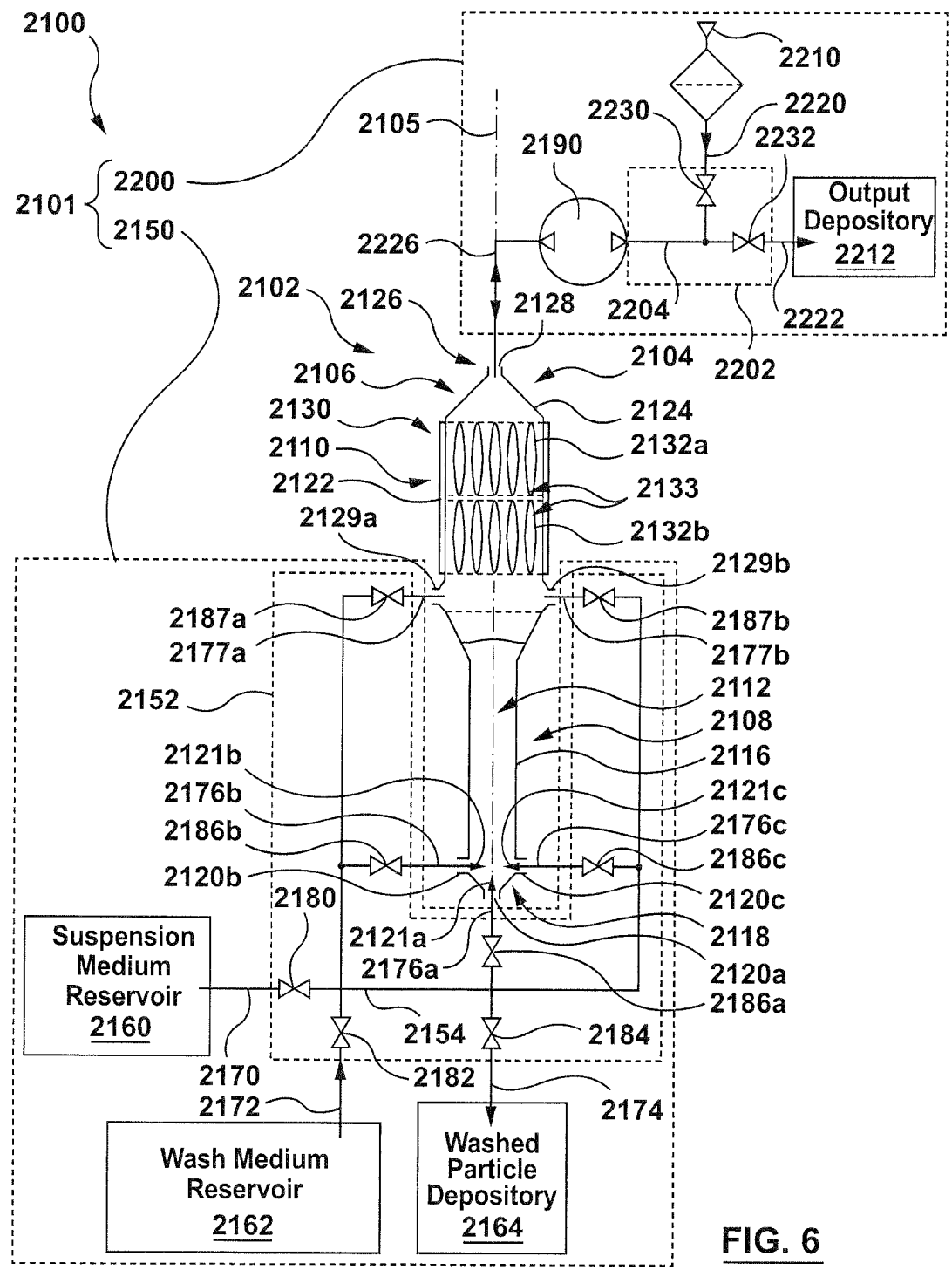
FIG. 6 is a schematic view of an alternative example acoustic chamber system for washing particles.

Referring to FIG. 6, an alternative example acoustic chamber system 2100 is illustrated. The acoustic chamber system 2100 has similarities to the acoustic chamber system 1100, and like features are identified by like reference characters, incremented by 1000.

In the example illustrated, the acoustic chamber system 2100 includes an acoustic chamber apparatus 2102. The acoustic chamber apparatus 2102 includes a chamber 2104 and a standing wave generating assembly 2130. In the example illustrated, when activated, the standing wave generating assembly 2130 generates a first standing wave 2132*a* and a second standing wave 2132*b* within a standing wave volume 2133 of the chamber 2104.

In the example illustrated, the chamber 2104 extends lengthwise along a chamber axis 2105. The chamber 2104 includes a chamber top portion 2106, an opposed chamber bottom portion 2108, and a chamber central portion 2110 extending between the chamber top and bottom portions 2106, 2108.

In the example illustrated, the chamber bottom portion 2108 includes a chamber bottom end 2118 of the chamber 2104 and a bottom portion sidewall 2116 extending upwardly from the bottom end 2118 to the chamber central portion 2110. In the example illustrated, the bottom portion sidewall 2116 is generally cylindrical. The chamber central portion 2110 has a central portion sidewall 2122 extending from the chamber bottom portion 2108 to the chamber top portion 2106. In the example illustrated, the chamber top portion 2106 has a top portion sidewall 2124 tapering upwardly from the chamber central portion 2110 toward a chamber top end 2126 of the chamber 2104. In the example illustrated, the chamber top portion 2106 is generally conical. In the example illustrated, the chamber top portion 2106 includes a top port 2128.

In the example illustrated, the chamber bottom portion 2108 defines a settling volume 2112 for accumulating particle concentrate. The settling volume 2112 can be shaped to facilitate formation of an expanded, spouted, or fluidized bed during flow of wash medium through particle concentrate within the settling volume 2112. This may reduce the amount of washing medium required to wash particles in the chamber 2104, and may improve efficiency of particle washing. In the example illustrated, the settling volume 2112 is below the standing wave volume 2133, and is defined by the bottom portion sidewall 2116. The bottom portion sidewall 2116 extends lengthwise along the chamber axis 2215, and has a diameter less than the diameter of the central portion sidewall 2122 to define an elongate, narrow settling volume 2112.

The chamber bottom portion 2108 can include at least one bottom port. In the example illustrated, the chamber bottom portion 2108 includes a first, second, and third bottom port 2120*a*, 2120*b*, 2120*c*, respectively, for directing flow of the wash medium into the settling volume 2112. In the example illustrated, the first bottom port 2120*a* is below the settling volume 2112. In the example illustrated, the bottom end 2118 of the chamber 2104 includes the first bottom port 2120*a*. The first bottom port 2120*a* directs flow of wash medium into the settling volume 2112 in a first flow direction 2121*a*.

In the example illustrated, the second and third bottom ports 2120*b*, 2120*c* are spaced apart from and above the first bottom port 2120*a*. In the example illustrated, the bottom portion sidewall 2116 includes the second and third bottom ports 2120*b*, 2120*c*. The second and third bottom ports 2120*b*, 2120*c* are on opposed sides of the bottom portion sidewall 2116 in the lower portion of the chamber bottom portion 2108 adjacent the bottom end 2118.

The second and third bottom ports 2120*b*, 2120*c* direct flow of wash medium into the settling volume 2112 in respective second and third flow directions 2121*b*, 2121*c*. The first, second, and third flow directions 2121*a*, 2121*b*, 2121*c* can be oriented at different angles from one another relative to the chamber axis 2105, or one or more of the first, second, and third flow directions 2121*a*, 2121*b*, 2121*c* can be oriented at the same angle relative to the chamber axis 2105. In the example illustrated, the first flow direction 2121*a* is generally coaxial with the chamber axis 2105. The second and third flow directions 2121*b*, 2121*c* are generally perpendicular to the chamber axis 2105, and diametrically opposed.

The chamber 2104 can further include at least one side port. In the example illustrated, the chamber central portion 2110 includes a first side port 2129*a* and a second side port 2129*b* above the settling volume 2112 and below the standing wave volume 2133. In the example illustrated, the first and second side ports 2129*a*, 2129*b* are at diametrically opposed sides of a lower portion of the central portion sidewall 2122 of the chamber 2104.

Figure 7:
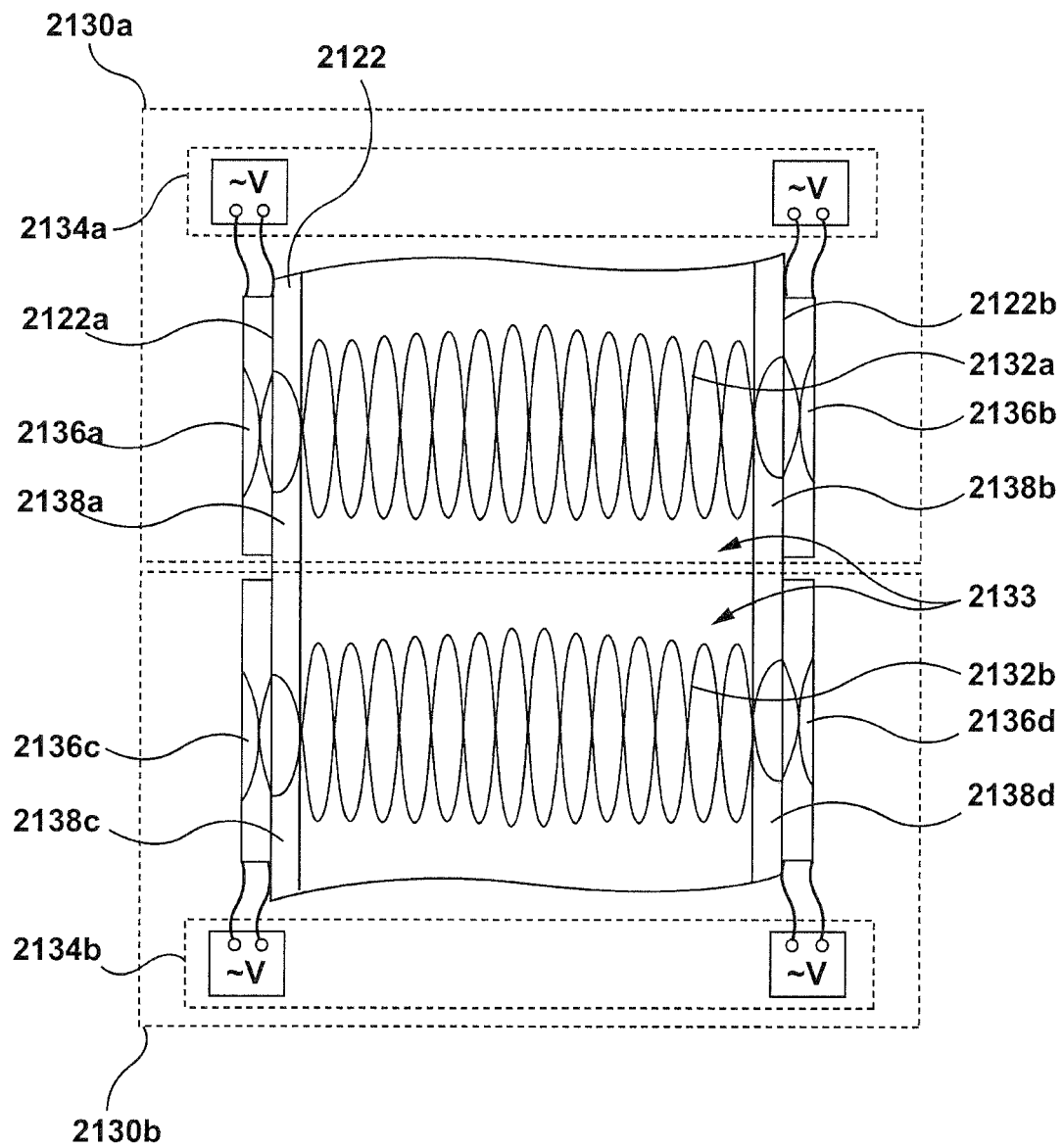
FIG. 7 is a schematic view of a standing wave generated in a standing wave volume of an acoustic chamber of the acoustic chamber system of FIG. 6.

Referring to FIG. 7, in the example illustrated, the standing wave generating assembly 2130 includes a first standing wave generating sub-assembly 2130*a*. When activated, the first standing wave generating sub-assembly 2130*a* generates the first standing wave 2132*a* in an upper sub-volume of the standing wave volume 2133. In the example illustrated, the first standing wave generating sub-assembly 2130*a* includes a first standing wave signal generator 2134*a* and two transducer plates 2136*a*, 2136*b* mounted on opposing parallel sides 2122*a*, 2122*b* of the central portion sidewall 2122 to provide two opposed transducing walls 2138*a*, 2138*b*. The first standing wave signal generator 2134*a* can provide a first driving signal to excite the opposed transducer plates 2136*a*, 2136*b* at matching frequencies. When the opposed transducers 2136*a*, 2136*b* are excited, the transducing walls 2138*a*, 2138*b* emit counter-propogating waves that superpose to form the first standing wave 2132*a*.

The standing wave generating assembly 2130 further includes a second standing wave generating sub-assembly 2130*b*. When activated, the second standing wave generating sub-assembly 2130*b* generates the second standing wave 2132*b* in a lower sub-volume of the standing wave volume 2133 below the first standing wave 2132*a*. In the example illustrated, the second standing wave generating sub-assembly 2130*b* includes a second standing wave signal generator 2134*b* and two transducer plates 2136*c*, 2136*d* mounted on the opposing parallel sides 2122*a*, 2122*b* of the central portion sidewall 2122 to provide two opposed transducing walls 2138*c*, 2138*d*. The second standing wave signal generator 2134*b* can provide a second driving signal to excite the opposed transducer plates 2136*c*, 2136*d* at matching frequencies. When the opposed transducers 2136*c*, 2136*d* are excited, the transducing walls 2138*c*, 2138*d* emit counter-propogating waves that superpose to form the second standing wave 2132*b*.

The standing wave volume 2133 is referred to herein as an "active" standing wave volume 2133 when either or both of the first and second standing wave generating sub-assemblies 2130*a*, 2130*b* are activated.

In the example illustrated, each of the first and second standing wave signal generators 2134*a*, 2134*b* can be configured to provide a different operating frequency for the respective first and second standing waves 2132*a*, 2132*b*. For example, the operating frequency of the second standing wave 2132*b* can be lower than the operating frequency of the first standing wave 2132*a*. The relatively lower operating frequency of the second standing wave 2132*b* can be optimized to retain and concentrate larger particles within the chamber 2104. The relatively higher operating frequency of the first standing wave 2132*a* can be optimized to retain and concentrate smaller particles within the chamber 2104.

In the example illustrated, the operating frequencies of the first and second standing waves 2132*a*, 2132*b* can be tuned toward individual resonance frequencies. This can help compensate for shifts in resonance frequencies within the respective upper and lower portions of the standing wave volume 2133 due to a change in the speed of sound within the chamber 2104 as the medium flowing through the chamber 2104 absorbs acoustic energy and warms up.

Referring back to FIG. 6, in the example illustrated, the acoustic chamber system 2100 further includes a fluid system 2101. The fluid system 2101 includes a first sub-system 2150 in fluid communication with a second sub-system 2200 via the chamber 2104.

In the example illustrated, the first sub-system 2150 includes a suspension medium reservoir 2160, a wash medium reservoir 2162, and a washed-particle depository 2164. In the example illustrated, the first sub-system 2150 further includes a first fluid manifold 2152 having a first header 2154. The first sub-system 2150 further includes a suspension medium line 2170; a wash medium line 2172; a washed-particle line 2174; first, second, and third bottom port lines 2176*a*, 2176*b*, 2176*c*; and first and second side port lines 2177*a*, 2177*b*.

In the example illustrated, the first, second, and third bottom port lines 2176*a*, 2176*b*, 2176*c* are coupled to the first, second, and third bottom ports 2120*a*, 2120*b*, 2120*c*, respectively, and can provide fluid communication between the first header 2154 and the settling volume 2112 of the chamber 2104. The first and second side port lines 2177*a*, 2177*b* are coupled to the first and second side ports 2129*a*, 2129*b*, and can provide fluid communication between the first header 2154 and an intermediate volume of the chamber 2104 above the settling volume 2112 and below the active standing wave volume 2133.

In the example illustrated, the first manifold 2152 includes a suspension medium valve 2180; a wash medium valve 2182; a washed-particle valve 2184; first, second, and third bottom port valves 2186*a*, 2186*b*, 2186*c* coupling the first, second, and third bottom port lines 2176*a*, 2176*b*, 2176*c*, respectively, to the first header 2154; and first and second side port valves 2187*a*, 2187*b* coupling the first and second side port lines 2177*a*, 2177*b*, respectively, to the first header 2154.

In the example illustrated, each of the first, second, and third bottom port valves 2186*a*, 2186*b*, 2186*c* is movable between an open position in which a respective first, second, and third bottom port line 2176*a*, 2176*b*, 2176*c* is in fluid communication with the first header 2154, and a closed position in which the respective first, second, and third bottom port line 2176*a*, 2176*b*, 2176*c* is in fluid isolation from the first header 2154. In the example illustrated, each of the first and second side port valve 2187*a*, 2187*b* is movable between an open position in which a respective first and second side port line 2177*a*, 2177*b* is in fluid communication with the first header 2154, and a closed position in which the respective first and second side port line 2177*a*, 2177*b* is in fluid isolation from the first header 2154.

In the example illustrated, the second sub-system 2200 includes a flush medium supply 2210 and an output depository 2212. The second sub-system 2200 further includes a second fluid manifold 2202, a flush medium line 2220, an output line 2222, a top port line 2226, and a fluid pump 2190. In the example illustrated, the second manifold 2202 includes a second header 2204, a flush medium valve 2230, and an output valve 2232.

In the example illustrated, the fluid system 2101 is configurable to a particle concentration condition, an evacuation condition, a fill condition, a wash condition, and a harvest condition.

In the example illustrated, when the fluid system 2101 is in the particle concentration condition, the pump 2190 is operated in the pump forward direction; the suspension medium valve 2180, the first and second side port valves 2187a, 2187b, and the output valve 2232 are in the open position; and the remaining valves are in the closed position. In the evacuation condition, the pump 2190 is operated in the pump reverse direction; the suspension medium valve 2180, the first and second side port valves 2187a, 2187b, and the flush medium valve 2230 are in the open position; and the remaining valves are in the closed position. In the fill condition, the pump 2190 is operated in the pump forward direction; the wash medium valve 2182, the first side port valves 2187a, 2187b, and the output valve 2232 are in the open position; and the remaining valves are in the closed position. In the wash condition, the pump 2190 is in the pump forward direction; the wash medium valve 2182, the first, second, and third bottom port valves 2186a, 2186b, 2186c, and the output valve 2232 are in the open position; and the remaining valves are in the closed position. In the harvest condition, the pump 2190 is operated in the pump reverse direction; the washed-particle valve 2184, the first bottom port valve 2186a, and the flush medium valve 2230 are in the open position; and the remaining valves are in the closed position.

Figure 8:
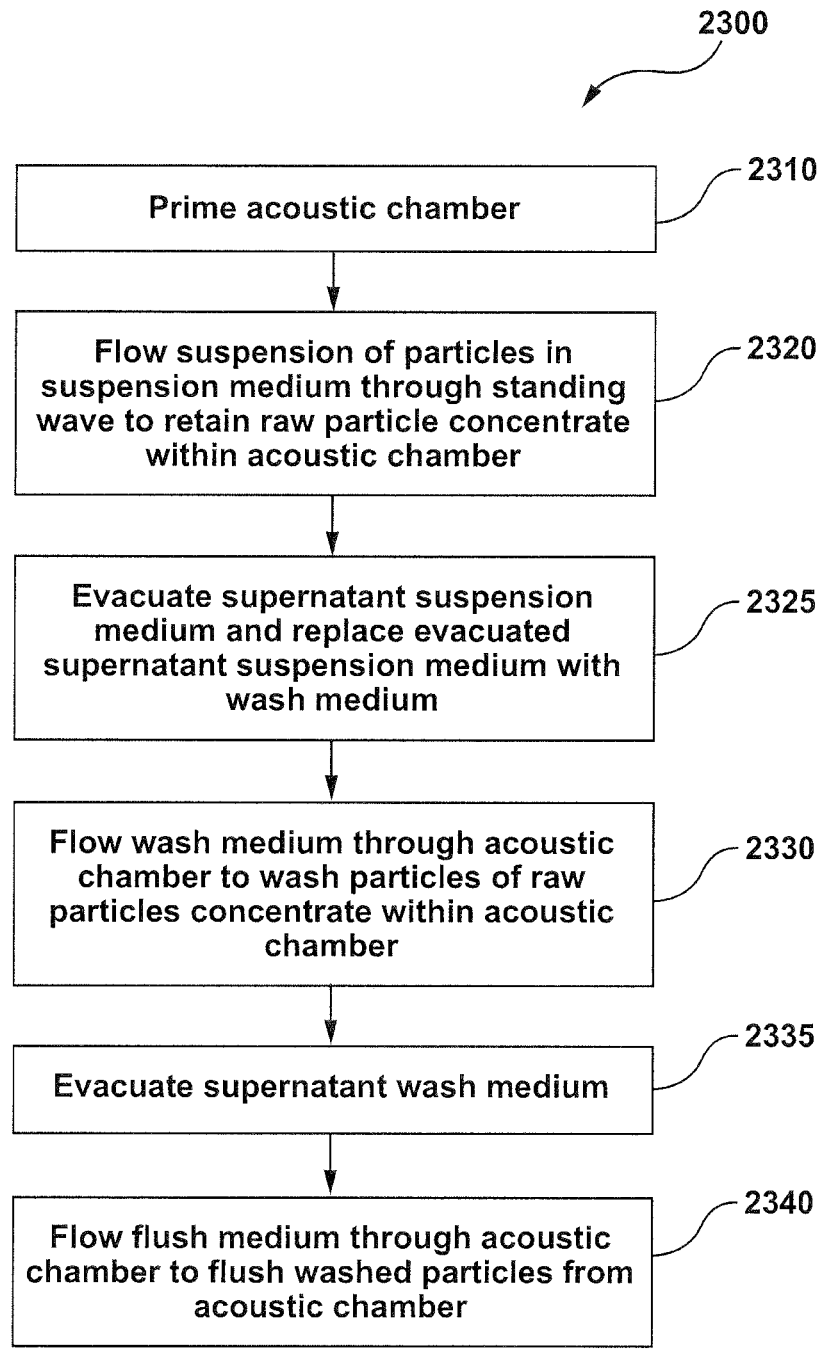
FIG. 8 is a flow chart illustrating an example particle washing method using the acoustic chamber system of FIG. 6.

Referring to FIG. 8, a particle washing method 2300 will be described. The particle washing method 2300 will be described with reference to the acoustic chamber system 2100. In alternative examples, the particle washing method 2300 may be carried out using other acoustic chamber systems, and the acoustic chamber system 2100 may be used according to other methods. The particle washing method 2300 has similarities to the particle washing method 1300, and like steps are identified by like reference characters, incremented by 1000.

At step 2310, the chamber 2104 can be primed with a medium.

At step 2320, the standing wave generating assembly 2130 is activated, the fluid system 2101 is configured to the particle concentration condition, and the particles suspended in the suspension medium flowing into the chamber 2104 are retained and concentrated within the chamber 2104 via the active standing wave volume 2133. In the particle concentration condition, the suspension medium flows from the suspension medium reservoir 2160 to the output depository 2212 through the suspension medium line 2170, the first header 2154, the first and second side port lines 2177a, 2177b, the first and second side ports 2129a, 2129b, the standing wave volume 2133, the top port 2128, the top port line 2226, the second header 2204, and the output line 2222. Flowing the suspension medium into the chamber 2104 through multiple side ports 2129 can allow for a reduction in flow speed while maintaining a suitable flow rate of the suspension medium, and can help reduce agitation of raw particle concentrate within the acoustic chamber. This may facilitate settling of the raw particle concentrate within the settling volume 2112.

Once a desired amount of the particles accumulates as raw particle concentrate in the settling volume 2112, the method 2300 can optionally proceed to step 2325. At step 2325, the fluid system 2101 is configured to the evacuation condition. In the evacuation condition, at least some of the supernatant suspension medium is evacuated from the chamber through the first and second side ports 2129a, 2129b. Once some of the supernatant suspension medium is evacuated, the fluid system 2101 can be configured to the fill condition to replace the evacuated supernatant suspension medium with the wash medium. In the fill condition, the wash medium flows from the wash medium reservoir 2162 into the chamber 2104 through the first and second side ports 2129a, 2129b.

At step 2330, the fluid system 2101 is configured to the wash condition to flow the wash medium in the fluid forward direction from the wash medium reservoir 2162 through the chamber 2104 to wash within the chamber 2104 at least some of the particles of the raw particle concentrate. In the example illustrated, at least some of the washed particles are retained within the chamber 2104 as washed particle concentrate during step 2330.

In the wash condition, the wash medium flows from the wash medium reservoir 2162 to the output depository 2212 through the wash medium line 2172; the first header 2154; the first, second, and third bottom port lines 2176a, 2176b, 2176c; the first, second, and third bottom ports 2120a, 2120b, 2120c; the settling volume 2112, the raw particle concentrate; the standing wave volume 2133; the top port 2128; the top port line 2226; the second header 2204; and the output line 2222.

Flowing the wash medium into the settling volume 2112 through multiple bottom ports 2120 can help increase agitation of the raw particle concentrate within the settling volume 2112, which may improve particle washing. It may also help prevent or inhibit the wash medium inflow stream from channeling through the raw particle concentrate without adequately washing the particles of the raw particle concentrate.

Optionally, each of the first, second, and third bottom port valves 2186a, 2186b, 2186c can be intermittently opened and closed during step 2330 to alternate the flow direction of the wash medium into the settling volume 2112. During a first time period, the first bottom port valve 2186a can be open and the remaining bottom port valves 2186b, 2186c can be closed to direct flow of the wash medium into the settling volume 2112 in the first flow direction 2121a. During a second time period, one or both of the second and third bottom port valves 2186b, 2186c can be opened to direct flow of the wash medium into the settling volume 2112 in the second flow direction 2121b and/or the third flow direction 2121c. The first bottom port valve 2186a can remain open during the second time period, or can be closed during the second time period.

In some examples, flow of the wash medium through the raw particle concentrate may resuspend some of the particles of the raw particle concentrate in the wash medium. The standing wave generating assembly 2130 may be activated at step 2330 to generate the standing wave 2132 if previously inactivated, and the wash medium and any resuspended particles may flow into the active standing wave volume 2133. As any resuspended particles flow into the active standing wave volume 2133, the particles form washed particle aggregates in antinodal areas of the standing wave 2132.

The washed particle aggregates can be retained within the chamber 2104 via the active standing wave volume 2133, while the wash medium flows out from the chamber 2104 to the output depository 2212 through the top port 2128. The washed particle aggregates can accumulate within the chamber 2104 as washed particle concentrate. In the example illustrated, when the washed particle aggregates become sufficiently large, the washed particle aggregates can settle under the force of gravity within the settling volume 2112.

After step 2330 and prior to step 2335, the fluid system 2101 can optionally be configured to the fill condition for a brief period to flush any particles within the first and second side port lines 2177a, 2177b and the first and second side ports 2129a, 2129b into the chamber 2104.

After step 2330 and prior to step 2340, the particle washing method can optionally proceed to step 2335. At step 2335, the fluid system 2101 is configured to the evacuation condition to evacuate at least some of the supernatant wash medium from the chamber 2104 through the first and second side ports 2129a, 2129b.

At step 2340, the standing wave generating assembly 2130 can be inactivated, and the fluid system 2101 is configured to the harvest condition. In the harvest condition, the flush medium flows through the chamber 2104 from the flush medium supply 2210 to flush the washed particle concentrate from the chamber 2104 into the washed-particle depository 2164 through the first bottom port 2120a.

Figure 9:
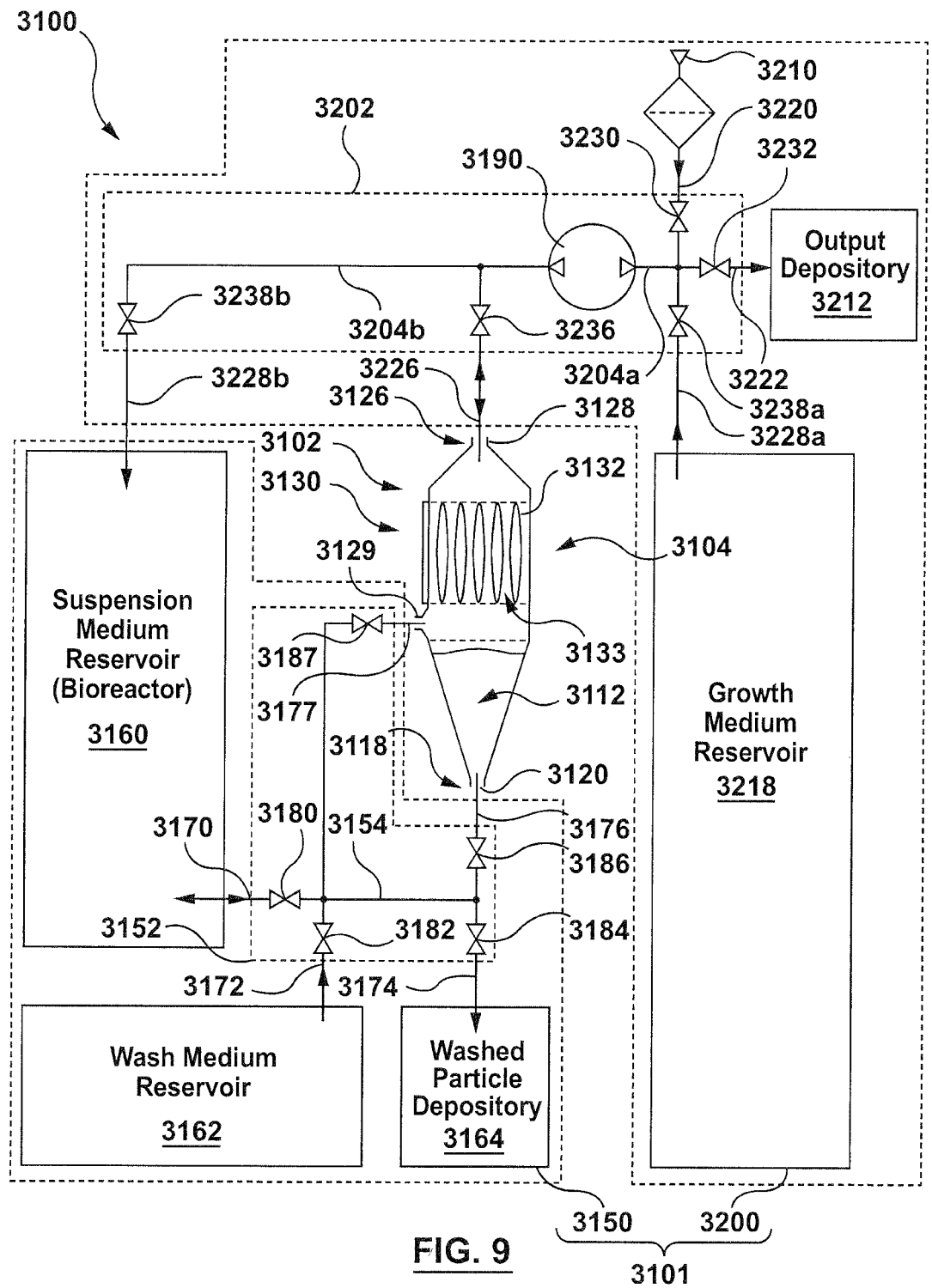
FIG. 9 is a schematic view of an alternative example acoustic chamber system for washing particles.

Referring to FIG. 9, an alternative example acoustic chamber system 3100 is illustrated. The acoustic chamber system 3100 has similarities to the acoustic chamber system 1100, and like features are identified by like reference characters, incremented by 2000. In the example illustrated, the acoustic chamber system 3100 is specialized for washing biological particles, such as, for example, perfused culture of cells grown in a bioreactor, and/or microcarriers of such cells.

In the example illustrated, the acoustic chamber system 3100 includes an acoustic chamber apparatus 3102. In the example illustrated, the acoustic chamber apparatus 3102 includes a chamber 3104 and a standing wave generating assembly 3130 for generating a standing wave 3132 within a standing wave volume 3133 of the chamber 3104. In the example illustrated, the standing wave volume 3133 is above a settling volume 3112 of the chamber 3104.

In the example illustrated, the chamber 3104 includes a bottom port 3120 below the settling volume 3112 at a bottom end 3118 of the chamber 3104, and a top port 3128 at a top end 3126 of the chamber 3104. In the example illustrated, the chamber 3104 further includes a side port 3129. In the example illustrated, the side port 3129 is above the settling volume 3112 and below the standing wave volume 3133.

In the example illustrated, the acoustic chamber system 3100 further includes a fluid system 3101. The fluid system 3101 includes a first sub-system 3150 in fluid communication with a second sub-system 3200 via the chamber 3104. The first sub-system 3150 includes a suspension medium reservoir 3160, a wash medium reservoir 3162, and a washed-particle depository 3164. In the example illustrated, the suspension medium reservoir 3160 includes a bioreactor for carrying out a culture process using a first growth medium and biological particles suspended in a suspension medium. The suspension medium reservoir 3160 is also referred to herein as a "first bioreactor 3160".

In the example illustrated, the first sub-system 3150 further includes a first fluid manifold 3152, a suspension medium line 3170, a wash medium line 3172, a washed-particle line 3174, a bottom port line 3176, and a side port line 3177. The first manifold 3152 includes a first header 3154, a suspension medium valve 3180, a wash medium valve 3182, a washed-particle valve 3184, a bottom port valve 3186, and a side port valve 3187.

In the example illustrated, the second sub-system 3200 includes a flush medium supply 3210, an output depository 3212, and a growth medium reservoir 3218 for storing a first growth medium. The second sub-system 3200 further includes a flush medium line 3220, an output line 3222, a top port line 3226, first and second growth medium lines 3228a, 3228b for supplying the first growth medium from the growth medium reservoir 3218, and a pump 3190.

In the example illustrated, the second sub-system 3200 further includes a second fluid manifold 3202 for directing and regulating fluid communication between the chamber 3104 and the flush medium supply 3220 and the output depository 3212, and for directing and regulating fluid communication between the growth medium reservoir 3218 and the first bioreactor 3160. The second sub-system 3200 includes a second header 3204a and a third header 3204b separated from the second header 3204a by the pump 3190.

In the example illustrated, the flush medium line 3220 can provide fluid communication between the flush medium supply 3210 and the second header 3204a. The output line 3222 can provide fluid communication between the output depository 3212 and the second header 3204a. The top port line 3226 is coupled to the top port 3128 and can provide fluid communication between the third header 3204b and the chamber 3104. The first growth medium line 3228a can provide fluid communication between the growth medium reservoir 3218 and the second header 3204a. The second growth medium line 3228b can provide fluid communication between the third header 3204b and the bioreactor 3160.

In the example illustrated, the second manifold 3202 further includes a flush medium valve 3230 coupling the flush medium line 3220 to the second header 3204a; an output valve 3232 coupling the output line 3222 to the second header 3204a; a first growth medium valve 3238a coupling the first growth medium line 3228a to the second header 3204a; a top port valve 3236 coupling the top port line 3226 to the third header 3204b; and a second growth medium valve 3238b coupling the second growth medium line 3228b to the third header 3204b.

In the example illustrated, each of the flush medium valve 3230, the output valve 3232, and the first growth medium valve 3238a is movable between an open position in which a respective flush medium line 3220, output line 3222, and first growth medium line 3228a is in fluid communication with the second header 3204a, and a closed position in which the respective flush medium line 3220, output line 3222, and first growth medium line 3228a is in fluid isolation from the second header 3204a. Each of the top port valve 3236 and the second growth medium valve 3238b is movable between an open position in which a respective top port line 3226 and second growth medium line 3228b is in fluid communication with the third header 3204b, and a closed position in which the respective top port line 3226 and second growth medium line 3228b is in fluid isolation from the third header 3204b.

In the example illustrated, the fluid pump 3190 is operable in a pump forward direction and a pump reverse direction. In the pump forward direction, the pump 3190 conducts fluid from the third header 3204b to the second header 3204a, and/or from the first sub-system 3150 to the second sub-system 3200 via the chamber 3104. In the pump reverse direction, the pump 3190 conducts fluid from the second header 3204a to the third header 3204b, and/or from the second sub-system 3200 to the first sub-system 3150 via the chamber 3104.

In the example illustrated, the fluid system 3101 is configurable to a particle concentration condition, a backflush condition, a feed condition, a wash condition, and a harvest condition.

In the example illustrated, when the fluid system 3101 is in the particle concentration condition, the pump 3190 is in the pump forward direction; the suspension medium valve 3180, the side port valve 3187, the top port valve 3236, and the output valve 3232 are in the open position; and the remaining valves are in the closed position. In the backflush condition, the pump 3190 is in the pump reverse direction; the flush medium valve 3230, the top port valve 3236, the bottom port valve 3186, and the suspension medium valve 3180 are in the open position; and the remaining valves are in the closed position. In the feed condition, the pump 3190 is in the pump reverse direction; the first growth medium valve 3238a and the second growth medium valve 3238b are in the open position; and the remaining valves are in the closed position. In the wash condition, the pump 3190 is in the pump forward direction; the wash medium valve 3182, the bottom port valve 3186, the top port valve 3236, and the output valve 3232 are in the open position; and the remaining valves are in the closed position. In the harvest condition, the pump 3190 is in the pump reverse direction; the flush medium valve 3230, the top port valve 3236, the bottom port valve 3186, and the washed-particle valve 3184 are in the open position; and the remaining valves are in the closed position.

Figure 10:
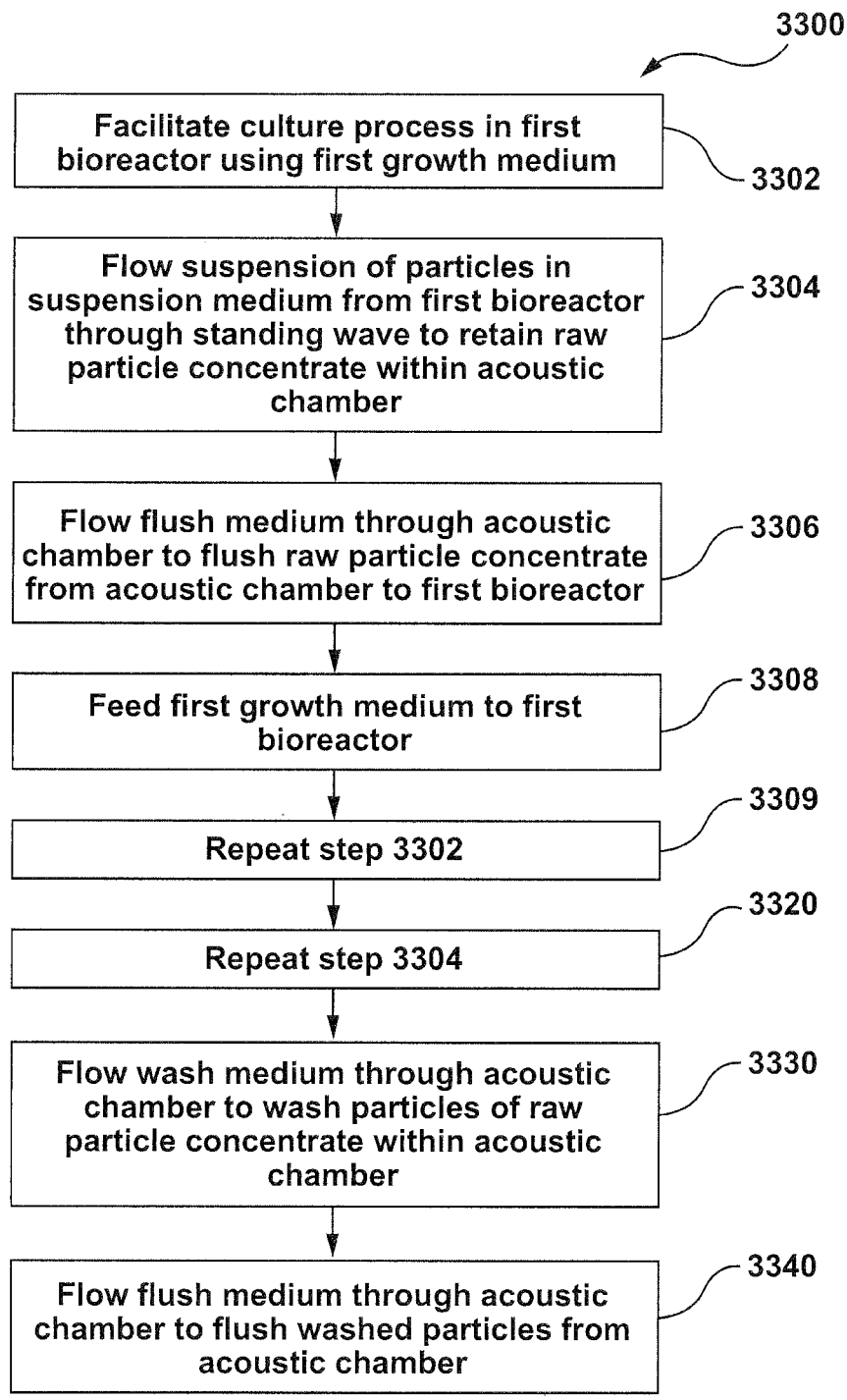
FIG. 10 is a flow chart illustrating an example particle washing method using the acoustic chamber system of FIG. 9.

Referring to FIG. 10, a particle washing method 3300 will be described. The method 3300 will be described with reference to the acoustic chamber system 3100. In alternative examples, the method 3300 may be carried out using other acoustic chamber systems, and the acoustic chamber system 3100 may be used according to other methods. The method 3300 has similarities to the method 1300, and like steps are identified by like reference characters, incremented by 2000.

At step 3302, a culture process is carried out in the first bioreactor using the first growth medium and the biological particles.

At step 3304, the standing wave generating assembly 3130 is activated and the fluid system 3101 is configured to the particle concentration condition. In the particle concentration condition, the suspension medium flows from the first bioreactor 3160 to the output depository 3212 through the suspension medium line 3170, the first header 3154, the side port line 3177, the side port 3129, the standing wave volume 3133, the top port 3128, the top port line 3226, the second and third headers 3204a, 3204b, and the output line 3222. The biological particles suspended in the suspension medium flowing into the chamber 3104 are retained within the chamber 3104 via the active standing wave volume 3133, and accumulate within the chamber 3104 as raw particle concentrate.

Once a desired amount of suspension medium has been drawn from the bioreactor 3160, the method 3300 can proceed to step 3306. At step 3306, the fluid system 3101 is configured to the backflush condition to flush the raw particle concentrate from the settling volume 3112 to the first bioreactor 3160 for use in a subsequent culture process. In the backflush condition, the flush medium flows from the flush medium supply 3210 to the first bioreactor 3160 through the flush medium line 3220, the second and third headers 3204a, 3204b, the top port line 3226, the top port 3128, and the settling volume 3112 to flush the raw particle concentrate through the bottom port 3120, the bottom port line 3176, the first header 3154, the suspension medium line 3170, and into the first bioreactor 3160.

At step 3308, the fluid system 3101 is configured to the feed condition to supply the first growth medium to the first bioreactor 3160 for use in the subsequent culture process. In the feed condition, the first growth medium flows from the growth medium reservoir 3218 to the bioreactor 3160 through the first growth medium line 3228a, the second and third headers 3204a, 3204b, and the second growth medium line 3228b. After step 3308 and prior to steps 3309 and 3320, steps 3302, 3304, 3306, and 3308 may be repeated for a desired number of cycles.

After step 3308, the method can proceed to step 3309. At step 3309, step 3302 is repeated. After step 3309, the method can proceed to step 3320. At step 3320, step 3304 is repeated.

Once a desired amount of the biological particles accumulates as raw particle concentrate within the chamber 3104 during step 3320, the particle washing method 3300 can proceed to step 3330. At step 3330, the fluid system 3101 is configured to the wash condition to flow the wash medium from the wash medium reservoir 3162 through the chamber 3104 to wash within the chamber 3104 at least some of the particles of the raw particle concentrate. In the example illustrated, at least some washed particles are retained within the chamber 3104 as washed particle concentrate during step 3330.

The standing wave generating assembly 3130 may be activated at step 3330 to generate the standing wave 3132 if previously inactivated. The wash medium and any resuspended biological particles may flow into the active standing wave volume 3133. The standing wave 3332 may retain any resuspended biological particles within the chamber 3104 as washed particle concentrate, while the wash medium flows out from the chamber 3104 to the output depository 3212 through the top port 3128. The washed particles can accumulate within the chamber 3104, and some may settle under the force of gravity within the settling volume 3112.

In the wash condition, the wash medium flows from the wash medium reservoir 3162 to the output depository 3212 through the wash medium line 3172, the first header 3154, the bottom port line 3176, the bottom port 3120, the raw particle concentrate, the settling volume 3112, the standing wave volume 3133, the top port 3128, the top port line 3226, the second and third headers 3204a, 3204b, and the output line 3222.

At step 3340, the standing wave generating assembly 3130 is inactivated, and the fluid system 3101 is configured to the harvest condition to flush the washed particle concentrate from the chamber 3104 and into the washed-particle depository 3164. In the harvest condition, the flush medium flows from the flush medium supply 3210 to the washed-particle depository 3164 through the flush medium line 3220, the second header 3204, the top port line 3226, the top port 3128, and the settling volume 3112 to flush the washed particle concentrate through the bottom port 3120, the bottom port line 3176, the first header 3154, the washed-particle line 3174, and into the washed-particle depository 3164.

In some examples, the washed-particle depository 3164 can include a second bioreactor. During step 3340, the washed particle concentrate can be flushed from the acoustic chamber 3304 into the second bioreactor. The second bioreactor can be filled with a second growth medium. The second growth medium can be different from the first growth medium. The second bioreactor can carry out a culture process using the second growth medium and the washed particles flushed into the second bioreactor.

In any of the above examples, various components may be disposable, such as the various reservoirs and depositories, the acoustic chamber, or the entire system. Alternatively, various components may be reusable.

In some examples, one or more of the mediums (e.g., the suspension medium and/or the wash medium) may have a density higher than that of the particles to be washed within one of the acoustic chamber systems described herein. This may cause the particles to float and/or rise within the acoustic chamber during use of the acoustic chamber system. To retain and/or wash particles in such examples, the acoustic chamber systems described herein can be flipped upside down, with the suspension medium and/or the wash medium flowing downwards through the acoustic chamber to concentrate and/or wash the particles, and the flush medium flowing upwards through the acoustic chamber to flush the particles from the acoustic chamber.

While the above description provides examples of one or more apparatuses, systems, or methods, it will be appreciated that other apparatuses, systems, or methods may be within the scope of the accompanying claims.

The invention claimed is:

1. A method of washing particles in an acoustic chamber, the method comprising:
 a) flowing a suspension of particles in a suspension medium through a standing wave generated in a standing wave volume of the acoustic chamber to accumulate within the acoustic chamber at least some of the particles as raw particle concentrate; and
 b) flowing a wash medium through the acoustic chamber to wash within the acoustic chamber at least some of the particles of the raw particle concentrate, and retaining within the acoustic chamber at least some washed particles;
 wherein some particles of the raw particle concentrate settle within a settling volume of the acoustic chamber, and wherein some of the washed particles settle within the settling volume, the settling volume located below the standing wave volume; and
 wherein the acoustic chamber includes a first bottom port below the settling volume and a top port above the standing wave volume, and wherein during step (b), the wash medium flows through the acoustic chamber from the first bottom port to the top port through the raw particle concentrate.

2. The method of claim 1, wherein during step (b) at least some of the settled washed particles and settled particles of the raw particle concentrate are resuspended in the wash medium as resuspended particles, and step (b) further comprises flowing the wash medium and the resuspended particles through the standing wave to retain the resuspended particles within the acoustic chamber.

3. The method of claim 1, wherein during step (a), the suspension medium flows through the acoustic chamber from the first bottom port to the top port through the standing wave.

4. The method of claim 1, wherein the acoustic chamber includes a side port above the settling volume, and wherein the method further comprises at least one of:
 i) during step a) flowing the suspension medium through the acoustic chamber from the side port to the top port through the standing wave; and
 ii) after step (a) and prior to step (b), evacuating at least some supernatant suspension medium from the acoustic chamber, and replacing the evacuated supernatant suspension medium with the wash medium, wherein the evacuated supernatant suspension medium is evacuated from the acoustic chamber through the side port and/or wherein the wash medium flows into the acoustic chamber through the side port to replace the evacuated suspension medium.

5. The method of claim 4, wherein the acoustic chamber includes at least one second bottom port spaced apart from the first bottom port, and wherein the method comprises at least one of i) in step (b), flowing the wash medium through the acoustic chamber from the second bottom port to the top port through the raw particle concentrate to facilitate loosening of the raw particle concentrate, and ii) during step b), introducing bubbles into the acoustic chamber from the first bottom port or the second bottom port through the raw particle concentrate to facilitate loosening of the raw particle concentrate.

6. The method of claim 4, further comprising at least one of (i) prior to step b), flushing the raw particle concentrate from the acoustic chamber into a line and pushing the raw particle concentrate from the line back into the acoustic chamber, to facilitate loosening of the raw particle concentrate and (ii) after step b), flushing the washed particles from the acoustic chamber into the line and then pushing the washed particles back into the acoustic chamber from the line, to facilitate loosening of the washed particles.

7. The method of claim 4, further comprising at least one of mechanically agitating the chamber, tilting the chamber, and flipping the chamber to facilitate loosening of the raw particle concentrate.

8. The method of claim 1, wherein a standing wave generating assembly generates the standing wave within the standing wave volume when activated and terminates generation of the standing wave when inactivated, and the method further comprises at least one of: (i) after step (a) and prior to step (b), inactivating the standing wave generating assembly to facilitate settling of the raw particle concentrate within the acoustic chamber, and (ii) after step (b), inactivating the standing wave generating assembly to facilitate settling of the washed particles within the acoustic chamber.

9. The method of claim 1, wherein:
 the particles are biological particles;
 step a) comprises flowing the suspension from a first bioreactor through the standing wave;
 the method further comprises (i) after step (a), flushing the raw particle concentrate from the acoustic chamber back to the first bioreactor, and filling the first bioreactor with a first growth medium;
 the method further comprises (ii) after step (i), repeating step (a);
 step b) is carried out after step (ii); and
 the method further comprises (iii) after step (b), flushing the washed particles from the acoustic chamber.

10. The method of claim 9, further comprising filling a second bioreactor with a second growth medium, wherein during step (iii) the washed particles are flushed from the acoustic chamber into the second bioreactor.

11. The method of claim 9, wherein step ii) comprises repeating step a) several times, and repeating step b) prior to each repetition of step a).

12. An acoustic chamber system for washing particles, the system comprising:
 a) an acoustic chamber;
 b) a standing wave generating assembly for generating a standing wave in a standing wave volume of the acoustic chamber; and
 c) a fluid system including a suspension medium line for supplying a suspension of the particles in a suspension medium from a suspension medium reservoir, and a wash medium line for supplying a wash medium from a wash medium reservoir, the fluid system configurable to:
  i. a particle concentration condition in which the suspension medium line and the acoustic chamber are in fluid communication for supplying the suspension medium to the standing wave volume, and
  ii. a wash condition in which the wash medium line and the acoustic chamber are in fluid communication for supplying the wash medium to a settling volume of the acoustic chamber, the settling volume below the standing wave volume;

wherein the acoustic chamber includes a bottom port below the settling volume, the bottom port providing fluid communication between the wash medium line and the settling volume when the fluid system is in the wash condition.

13. The system of claim 12, wherein the wash medium line and the acoustic chamber are in fluid isolation from each other when the fluid system is in the particle concentration condition, and wherein the suspension medium line and the acoustic chamber are in fluid isolation from each other when the fluid system is in the wash condition.

14. The system of claim 12, wherein the bottom port provides fluid communication between the suspension medium line and the settling volume when the fluid system is in the particle concentration condition.

15. The system of claim 12, wherein the acoustic chamber includes a side port above the settling volume, the side port providing fluid communication between the suspension medium line and the acoustic chamber when the fluid system is in the particle concentration condition.

16. The system of claim 15, wherein the fluid system is configurable to a combined condition in which the suspension medium line and the acoustic chamber are in fluid communication for supplying the suspension medium to the standing wave volume through the side port, and at the same time the wash medium line and the acoustic chamber are in fluid communication for supplying the wash medium to the settling volume through the bottom port.

17. An acoustic chamber apparatus for washing particles, the apparatus comprising:

a) an acoustic chamber including:
   i. a chamber bottom portion defining a settling volume for accumulating a particle concentrate of the particles, the chamber bottom portion having a first bottom port below the settling volume, the first bottom port for directing flow of a wash medium into the settling volume, and
   ii. a chamber top portion vertically spaced from the chamber bottom portion and having a top port for evacuating the wash medium from the acoustic chamber; and
b) a standing wave generating assembly for generating a standing wave in a standing wave volume of the acoustic chamber, the standing wave volume above the settling volume and below the top port;

wherein the acoustic chamber further includes a side port above the settling volume, the side port configured to direct flow of a suspension of the particles in a suspension medium into the acoustic chamber for supplying the suspension medium to the standing wave volume; and wherein the side port is configured to direct fluid into the acoustic chamber in a generally horizontal direction.

18. The apparatus of claim 17, wherein the apparatus further comprises at least one second bottom port spaced apart from the first bottom port, the first bottom port is configured to direct flow of the wash medium into the settling volume in a first direction, the second bottom port is configured to direct flow of the wash medium into the settling volume in a second direction different from the first direction, and the chamber bottom portion comprises a bottom end of the acoustic chamber and a side wall extending upwardly from the bottom end, the bottom end comprising the first bottom port and the side wall comprising the second bottom port.

* * * * *